(12) United States Patent
Chen et al.

(10) Patent No.: US 7,247,300 B1
(45) Date of Patent: Jul. 24, 2007

(54) THERAPEUTIC USE OF SOLUBLE CD39L3

(75) Inventors: Ridong Chen, Naperville, IL (US);
Soon S. Jeong, St. Louis, MO (US);
Timothy A. Mitsky, Maryland Heights, MO (US)

(73) Assignee: APT Therapeutics, Inc., St. Louis, MO (US)

( * ) Notice: Subject to any disclaimer, the term of this patent is extended or adjusted under 35 U.S.C. 154(b) by 531 days.

(21) Appl. No.: 10/703,780

(22) Filed: Nov. 7, 2003

Related U.S. Application Data

(60) Provisional application No. 60/425,316, filed on Nov. 7, 2002.

(51) Int. Cl.
*A61K 38/46* (2006.01)

(52) U.S. Cl. ............... 424/94.6; 514/2; 514/12; 435/7.1; 435/69.1; 530/350; 530/300

(58) Field of Classification Search ............... None
See application file for complete search history.

(56) References Cited

U.S. PATENT DOCUMENTS 6,787,328 B1 * 9/2004 Chadwick et al. ............ 435/21

FOREIGN PATENT DOCUMENTS

WO  WO 00/23459  4/2000
WO  WO 01/11949  2/2001

OTHER PUBLICATIONS

Wells, Biochemistry, vol. 29, pp. 8509-8517, 1990.*
Seffernick et al., J. Bacteriology, vol. 183, pp. 2405-2410, 2001.*
Guo et al., PNAS, vol. 101, No. 25, pp. 9205-9210, 2004.*
Bairoch et al., Nucleic Acids Res (2000) 28:45-48.
Chadwick et al., Genomics (1998) 50:357-367.
Chiu et al., Stroke (1998) 29:18-22.
Clifford et al., Am. J. Physiol. (1997) 42:C973.
Dzhandzhugazyan et al., FEBS Lett (1998) 430:227.
Gayle et al., J. Clin. Invest (1998) 101:1851-1859.
Gendron et al., Curr Drug Targets (2002) 3:229.
Haber et al., Science (1989) 243:51-56.
Kaczmarek et al., J. Biol. Chem. (1996) 271:33116-33122.
Maliszewski et al., J. Immunol. (1994) 153:3574.
Marcus et al., FASEB J. (1993) 7:516-522.
Marcus et al., J. Clin. Invest. (1997) 99:1351-1360.
Marcus et al., Ital. Heart J. (2001) 2:824-830.
Runge et al., Circulation (1989) 79:217-224.
Smith and Kirley, Biochemica et Biophysica Acta (1998) 1386:65-78.
Thompson et al., Nucleic Acids Res (1994) 22:4673-4680.
Wang, Mol. Brain Res. (1997) 47:295.
Wardlaw et al., Lancet (1997) 350:607-614.
Zimmermann, Tips (1999) 20:231-236.

* cited by examiner

*Primary Examiner*—Hope Robinson
(74) *Attorney, Agent, or Firm*—Morrison & Foerster LLP

(57) ABSTRACT

The present invention provides soluble forms of CD39L3 polypeptides and compositions, and methods useful inhibiting platelet activation and recruitment for the treatment and prevention of thrombotic disorders in mammals administered with soluble forms of CD39L3 polypeptides.

15 Claims, 16 Drawing Sheets

Figure 2.

| Enzyme | CD39 | CD39L3 |
| --- | --- | --- |
| No of AA | 517 | 529 |
| MW (Daltons) | 57964.5 | 59133.2 |
| pI | 6.29 | 6.23 |
| Ala (A) | 5.4% | 6.6% |
| Arg (R) | 2.5% | 2.8% |
| Asn (N) | 4.1% | 4.5% |
| Asp (D) | 3.5% | 3.6% |
| Cys (C) | 2.1% | 2.5% |
| Gln (Q) | 6.0% | 4.7% |
| Glu (E) | 6.2% | 5.3% |
| Gly (G) | 6.8% | 6.6% |
| His (H) | 2.1% | 3.0% |
| Ile (I) | 6.2% | 4.7% |
| Leu (L) | 9.7% | 9.3% |
| Lys (K) | 6.4% | 4.3% |
| Met (M) | 2.3% | 1.9% |
| Phe (F) | 6.2% | 6.0% |
| Pro (P) | 4.1% | 5.1% |
| Ser (S) | 7.2% | 8.7% |
| Thr (T) | 6.2% | 6.6% |
| Trp (W) | 1.5% | 1.5% |
| Tyr (Y) | 5.2% | 4.9% |
| Val (V) | 6.4% | 7.2% |

Figure 3.

```
              10         20         30         40         50         60         70
               |          |          |          |          |       ACR1  |
hCD39     MKGTKDLTSQQKESNVKTFCSKNILAILG-FSSIIAVIALLAVGLTQNKALPENVKYGIVLDAGSSHTSL
hCD39L3   MFTVLTRQPCEQAGLKALYRTPTIIALVVLLVSIVVLVSITVIQIHKQEVLPPGLKYGIVLDAGSSRTTV 80         90        100        110        120        130        140
               |          |          |          |          |          |    ACR2 |
hCD39     YIYKWPAEKENDTGVVHQVEECRVKGPGISKFVQKVNEIGIYLTDCMERAREVIPRSQHQETPVYLGATA
hCD39L3   YVYQWPAEKENNTGVVSQTFKCSVKGSGISSYGNNPQDVPRAFEECMQKVKGQVPSHLHGSTPIHLGATA 150        160        170        180        190        200        210
               |          |          |          |   ACR3   |          |          |
hCD39     GMRLLHMESEELADRVLDVVERSLSNYPFDFQGARIITGQEEGAYGWITINYLLGKFSQKTRWFSIVPYE
hCD39L3   GMRLLHLQNETAANEVLESIQSYFKSQPFDFRGAQIISGQEEGVYGWITANYLMGNFLEKNLWHMWV--H 220        230        240        250        260        270        280
             |  ACR4    |          |          |          |          |          |
hCD39     TNNQETFGALDLGGASTQVTFVPQNQTIESPDNALQFRLYGKDYNVYTHSFLCYGKDQALWQKLAKDIQ-
hCD39L3   PHGVETTGALDLGGASTQISFVAGEKMDLNTSDIMQVSLYGYVYTLYTHSFQCYGRNEAEKKFLAMLLQN 290        300        310        320        330        340        350
               |          |          |          |          |          |          |
hCD39     VASNEILRDPCFHPGYKKVVNVSDLYKTPCTK--RFEMTLPFQQFEIQGIGNYQQCHQSILELFNTSYCP
hCD39L3   SPTKNHLTNPCYPRDYSISFTMGHVFDSLCTVDQRPESYNPNDVITFEGTGDPSLCKEKVASIFDFKACH 360        370        380        390        400        410        420
               |          |          |          |          |          |          |
hCD39     -YSQCAFNGIFLPPLQGDFGAFSAFYFVMKFLNLTSEKVSQEKVTEMMKKFCAQPWEEIKTSYAGVKEKY
hCD39L3   DQETCSFDGVYQPKIKGPFVAFAGFYYTASALNLS-GSFSLDTFNSSTWNFCSQNWSQLPLLLPKFDEVY 430        440        450        460        470        480        490
               |          |          |     ACR5  |          |          |          |
hCD39     LSEYCFSGTYILSLLLQGYHFTADSWEHIHFIGKIQGSDAGWTLGYMLNLTNMIPAEQPLS-----TPLS
hCD39L3   ARSYCFSANYIYHLFVNGYKFTEETWPQIHFEKEVGNSSIAWSLGYMLSLTNQIPAESPLIRLPIEPPVF 500        510        520        530
               |          |          |          |
hCD39     HSTYVFLMVLFSLVLFTVAIIGLLIFHK--PSYFWKDMV---
hCD39L3   VGTLAFFTVAALLCLAFLAYLCSATRRKRHSEHAFDHAVDSD
```

Figure 11.

Signal
                               cleavage
           *Igκ leader sequence*            ↓

ATG GAG ACA GAC ACA CTC CTG CTA TGG GTA CTG CTG CTC TGG GTT CCA GGT TCC ACT GGT / GAC
Met Glu Thr Asp Thr Leu Leu Leu Trp Val Leu Leu Leu Trp Val Pro Gly Ser Thr Gly / Asp

Srf I
GC<u>G CCC / GGG C</u>CG ...
Ala Pro Gly

Figure 15.

|  | ATP | | | ADP | | | $(V/K)^{atp}/(V/K)^{adp}$ |
| --- | --- | --- | --- | --- | --- | --- | --- |
|  | $K_m (\mu M)^{ATP}$ | $V_{max} (x10^{-4} s^{-1})^{ATP}$ | $V_{max}/K_m$ | $K_m (\mu M)^{ADP}$ | $V_{max} (x10^{-4} s^{-1})^{ADP}$ | $V_{max}/K_m$ |  |
| sol-CD39 | 3.48 | 0.25 | 0.0706 | 11.00 | 0.35 | 0.0315 | 2.24 |
| sol-CD39L3 | 135.93 | 14.11 | 0.1038 | 134.09 | 4.67 | 0.0348 | 2.98 |

THERAPEUTIC USE OF SOLUBLE CD39L3

CROSS-REFERENCE TO RELATED APPLICATION

This application claims benefit to U.S. Provisional Application No. 60/425,316, filed 7 Nov. 2002. The contents of this document are incorporated herein by reference.

TECHNICAL FIELD

The invention relates to use of certain ADPases for the prevention and or treatment of thrombotic or ischemic disorders, for example, stroke.

BACKGROUND ART

Thrombosis is the formation, development, or existence of a blood clot or thrombus within the vascular system. This is a life saving event when occurs during hemorrhage and a life threatening event when it occurs at any other time. Occlusion of a blood vessel, caused by excessive platelet activation (by the stimulation of an agonist) and recruitment (leading to platelet aggregation and vessel occlusion), are the major contributing factors in clinical disorders such as stroke, myocardial infarction, unstable angina, and restenosis. Therefore, there is a great need to identify therapeutic strategies and compositions for the pharmacological neutralization of platelet reactivity (activation, recruitment, and aggregation).

Currently, several treatment strategies are available to deal with a thrombus formation and fall into two classes, protein based therapeutics and small molecule therapeutics. The classes of treatments cover several therapeutic approaches such as: acting as anti-coagulants (for example, heparin and hirudin), thrombolytic agents (for example, tPA, pro-urokinase, and Streptokinase) or antiplatelet agents (for example, aspirin, ticlopidine, and clopidogel). However, their therapeutic utility is limited due to a significant risk of bleeding complications (Wardlaw, J. M., et al., *Lancet* (1997) 350:607-614). For example, in the United States, less than 2% of the patients with acute ischemic stroke can receive rtPA due to intracranial hemorrhage risks (Chiu, D., et al., *Stroke* (1998) 29:18-22). Glycoprotein IIb/IIIa antagonists such as ReoPro® (monoclonal antibody) have been used for percutaneous coronary intervention (PCI) and are currently under clinical investigation for the treatment of patients with acute coronary syndromes and acute ischemic stroke. However, the inhibition of the glycoprotein IIb/IIIa receptors will interfere with platelet adhesion resulting in bleeding complications. Therefore, it is important to identify novel, strategies, for inhibition of platelet function that will significantly reduces the risks of bleeding.

During early stages of platelet activation, several agonists including ADP, Thromboxane $A_2$ and serotonin are released. Among these, ADP is the single most important platelet agonist and recruiting agent that is present in the thrombus microenvironment (Marcus, A. J. and Safier, L. B., *FASEB J.* (1993) 7:516-522). Part of the normal function of endothelial cells ability to maintain blood fluidity is the local generation of an enzyme with ectoapyrase (apyrase, ATP diphosphohydrolase, ATP-diphosphatase, Adenosine diphosphatase, ADPase, E-NTPDase, EC 3.6.1.5) activity such as CD39. CD39 is a constitutively expressed enzyme having apyrase activity that strongly inhibits platelet aggregation by rapidly metabolizing ADP released from activated platelets, thus terminating further platelet recruitment and aggregation. (Marcus, A. J., et al., *J. Clin. Invest.* (1997) 99:1351-1360; Gayle, R., et al., *J. Clin. Invest* (1998) 101:1851-1859). Several research studies have now established CD39 as the prime thromboregulator (Marcus, A. J., et al., *J. Clin. Invest.* (1997) 99:1351-1360; Kaczmarek, E., et al., *J. Biol. Chem.* (1996) 271:33116-33122). In addition, animal model studies indicate that administration of a soluble form of CD39 for treatment has significant clinical advantages over existing treatment regimes without the life threatening side effects often associated with the current treatment strategies (PCT WO 01/11949; PCT WO 00/23459).

This invention is directed to the use of CD39L3, brain specific isoenzyme of CD39, useful for the inhibition of platelet activation and as a general thromboregulator useful for the treatment and prevention of stroke and other diseases involving thrombosis. More specifically it encompasses the use of a soluble form of CD39L3.

DISCLOSURE OF THE INVENTION

The invention is directed to methods to ameliorate or protect against thrombotic disorders by administering CD39L3 or a soluble form thereof. The soluble form may be supplied as a fusion protein; indeed other CD39 family members can be supplied as fusion proteins as well. In one embodiment, the fused sequence targets the soluble CD39 to a thrombus.

Also included in the invention are altered forms of CD39 that enhance ADPase activity and/or diminish unwanted related activities; also included are altered forms that are more efficiently expressed in recombinant production.

Similarly, the nucleotide sequences encoding the above mentioned proteins are within the scope of the invention; in some instances, treatment can be effected by administering expression systems for these proteins.

BRIEF DESCRIPTION OF THE DRAWINGS

FIG. 2 is a comparison of the protein physiochemical properties of Human CD39 and CD39L3.

FIG. 3 is the pairwise sequence alignment of human (h) hCD39 (GenBank P49961) (SEQ. ID. NO: 26) and hCD39L3 (GenBank O75355) (SEQ. ID. NO: 27). Apyrase conserved regions (ACRs) are in dotted boxes. Conserved cysteines are identified by a double underline. Sequences for adenine binding moiety are in italic and underlined. Each exon region is alternatively shaded indicating genes have originated from divergent evolution.

FIG. 11 is a graphic representation of the IgK leader sequence with the introduced Srf I restriction enzyme used to translationally fuse the sol-CD39L3 gene (SEQ ID NO:23). Proper post-translational processing of the signal peptide will introduce an Asp-Ala-Pro-Gly (SEQ ID NO:30) to the N-terminus of the sol-CD39L3 peptide.

FIG. 15 is a table of the kinetic parameters for ADPase activity and ATPase activity of soluble CD39 and soluble CD39L3.

MODES OF CARRYING OUT THE INVENTION

Hemostasis and Thromboregulation

Figure 1:
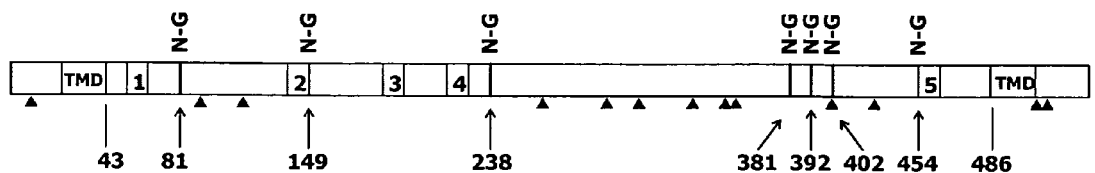
FIG. 1 shows the some key structural features of CD39L3. The two transmembrane domains are labeled as TMD located at both the N- and C-termini. The Five ACRs regions are labeled as 1 to 5. The putative N-glycosylation sites are marked with the corresponding residue numbers (SEQ ID NO:20) and labeled as N-G. Cysteines are also marked as triangles.

The hemostatic process represents a series of physiological and biological processes that culminate in the arrest of hemorrhage from blood vessels that have been severed or mechanically traumatized. Hemostasis is accomplished by the action of multiple systems including endothelial cells, blood platelets, and plasma proteins of the intrinsic and extrinsic coagulation systems. Disorders in any or all of the systems can result in defective hemostasis or coagulation resulting in mild to severe hemorrhagic diathesis (Marcus, A J (1996) In:Ratnoff, O. D. and Forbes, C. D., eds. *Disorders of Hemostasis*, 3$^{rd}$ ed. Philadelphia: W B Saunders, 79-137). The efficiency of the hemostatic process serves as an agonist for unwanted activation of hemostasis and promotion of blood coagulation. This action results in the misdirected culmination of arterial or venous thrombosis at critical circulation sites such as the coronary or cerebral circulation systems.

Primary hemostatic events occur during interruption of blood vessel continuity by exposure of the subendothelial matrix and more specifically exposed collagen. The exposed collagen is an immediate attractor and agonist of circulating platelet cells (the keystone of the hemostatic arch) and von Willebrand's factor (vWF). During high sheer stress, occurring in small blood vessels or larger vessels with a partial occlusion, vWF plays an extremely important role in generation of the platelet plug. Platelet recruitment is the critical step in the formation of a thrombus and ultimately results in the total occlusion of the vessel by the platelet thrombus. This recruitment is possible by the release of several factors by the platelet including ADP, thromboxane $A_2$, serotonin (5-HT), lysosomal enzymes and growth factors including platelet factor 4. Of these factors ADP has been established as the primary agonist for further platelet recruitment.

Thromboregulation is defined as a group of processes by which circulating blood cells and cells of the blood vessel wall interact to regulate the formation and development of a thrombus. Thromboregulators are mainly responsible for maintaining blood fluidity and can be classified according to their chronological mode of action in relation to thrombin formation. They can prevent or reverse platelet accumulation, activate coagulation factors, and induce fibrin formation as a result of a hemostatic process. Early thromboregulators such as nitric oxide (NO), Eicosanoids (prostacyclin, $PGD_2$) and ecto-ADPase (CD39) inhibit events preceding thromus formation. Late thromboregulators such as antithrombin III, heparin proteoglycans, tissue factor pathway inhibitor (TFPI), thrombomodulin-protein-C-protein S pathway, and fibrinolytic proteins exhibit effects after thrombin formation. Many of these defense systems can be overwhelmed by the agonistic activities resulting from vascular injury.

CD39 is the Key Thromboregulator

ADP is the most critical agonist of platelet aggregation present in the activated platelet releasates. Hydrolysis (metabolism or catabolism) of ADP to AMP by the action of the thromboregulatory ecto-ADPase (such as CD39) blocks further recruitment and activation of additional platelets to the thrombus site and effectively reverses the aggregation response and blocks further thrombus formation. CD39 (cluster of differentiation 39) is a cell surface molecule that is recognized by a cluster of monoclonal antibodies that are useful in distinguishing one class of lymphocytes from another. CD39 is a 510 amino acid peptide (also reported as a 517 amino acid peptide Genbank: gi:21361569)) with a predicted mass of 57 kDa. However, CD39 displays a molecular mass of approximately 100 kDa due to extensive N-glycosylation (Maliszewski, C. R., et al., *J. Immunol.* (1994) 153:3574). CD39 contains two hydrophobic transmembrane domains located at the N-terminus and C-terminus. Recently, a truncated form of CD39 resulting in a soluble peptide retaining the same nucleotidase activity as the wild type was produced by removing the hydrophobic transmembrane domains at both the N-terminus and C-terminus (Gayle, R. B., et al., *J. Clin Invest.* (1998) 191:1851). It has also been demonstrated that the soluble form of CD39 is capable of blocking ADP induced platelet aggregation and inhibit collagen-induced platelet reactivity in vitro. (Gayle, R. B., et al., *J. Clin. Invest.* (1998) 101:1851-1859). In vivo studies with CD39 null (CD39–/–) mice have also indicated that administration of the soluble form of CD39 is an effective therapeutic agent for thrombotic stroke. (Marcus, A. J., et al., *Ital. Heart J.* (2001) 2:824-830.)

CD39 is a member of the E-NTPase protein family that hydrolyse either nucleoside 5'-triphosphates or both nucleoside-5'-tri- and diphosphates. Currently there are several vertebrate members of the E-NTPase gene family that are grouped according to their phylogenetic relationships. These include but are not limited to CD39, CD39L1, CD39L2, CD39L3, CD39L4, and CD39L5. In addition the membrane topography of the currently known mammalian members of the E-NTPase family have been characterized. (Zimmermann, H., *Tips* (1999) 20:231-236).

CD39L3 is an Isozyme of CD39

Among the known human CD39 family, CD39L3 is known as an ecto-apyrase (ecto-ATPDase) with biochemical activity between CD39 (ecto-ATDPase) and CD39L1 (ecto-ATPase). Smith and Kirley (*Biochemica et Biophysica Acta*, (1998) 1386:65-78) determined CD39L3 is found primarily in human brain tissue, although the precise biological and biochemical function of CD39L3 have not been elucidated.

Specifically CD39L3 is a 529 amino acid protein with a predicted molecular weight of 59132.42 Daltons. The isoelectric point of CD39L3 is 6.233. There are seven putative glycosylation sites and 13 cysteine residues. Based on SEQ ID NO:20, the N-terminal 43 residues and C-terminal 44 residues are considered to be part of a transmembrane domain. The catalytic core of the enzyme roughly resides between amino acid 44 through amino acid 238 (FIG. 1).

ProtParam analysis shows that both CD39L3 and CD39 are composed of about 520 amino acids with the pI of about 6.0 (FIG. 2). CD39L3 and CD39 also share similar amino acid compositions to each other and common structural motifs including about 440 amino acid residues of the extracellular APTDase portion that resides between the N- and C-terminal transmembrane regions. Although CD39L3 is found in chromosome 3 and CD39 in chromosome 10, their overall intron and exon structures are identical with 10 exons each.

Pairwise sequence alignment of CD39L3 and CD39 shows about 35% sequence identity. Although the overall sequence identity is low the key amino acid residues involved in catalysis, substrate binding and structural motifs are highly conserved. For example, the majority of the sequence identity between CD39L3 and CD39 can be accounted for conservation in the apyrase conserved regions (ACRs). ACRs determine the number of phosphates hydrolyzed from the substrate nucleotides (FIG. 3). In addition, key residues between ACR4 and ACR5 (FIG. 3) that specify base binding (for example, adenine) are conserved and residues for structure formation (such as Cys, Pro, and Gly) are also conserved (FIG. 3).

Bioinformatics analysis (Example 1) suggests that CD39L3 is a brain specific isozyme or isoenzyme of CD39. Isozymes or isoenzymes may not have the same regulatory properties as their respective counterpart, but rather have adjusted their enzymatic properties to be optimal for the precise environment to which they are subject. Northern blot studies showed CD39L3 is highly expressed in brain and kidney, while CD39 is expressed in placenta and spleen. Based on the analysis it suggests that expression of the isoenzyme CD39L3 in human brain complements the activity of CD39 as the key thromboregulator. Since catalytic properties of CD39L3 and CD39 have not been properly determined or compared in the literature, their catalytic properties (such as $K_m$, $k_{cat}$, $k_{cat}/K_m$) are determined to make stringent kinetic comparisons.

Utility of CD39L3

Agents that regulate the process of thrombosis, especially platelet aggregation have utility in treating occlusive vascular diseases. CD39L3 is the isozyme of the ecto-ADPase (apyrase) CD39. Because ADP is the most important agonist of platelet aggregation, and is present in activated platelet releasate, an agent that metabolizes ADP is useful for treating disease involving inappropriate activation and aggregation of platelets. The present invention is directed to the use of CD39L3, more preferably the use of a biologically active soluble form of CD39L3 for the treatment and prevention of thrombotic disorders.

Examples of therapeutic uses of CD39L3 and biologically active derivatives include but are not limited to, for example, treatment of individuals who suffer from stroke, coronary artery disease or injury resulting from myocardial infarction, atherosclerosis, arteriosclerosis, embolism, preeclampsia, angioplasty, vessel injury, transplantation, neonatal hypoxic ischemic encephalopathy, platelet-associated ischemic disorders including lung ischemia, coronary ischemia and cerebral ischemia, thrombotic disorders including, coronary artery thrombosis, cerebral artery thrombosis, intracardiac thrombosis, peripheral artery thrombosis, and venous thrombosis.

Other examples in which it would be useful to inhibit ADP induced platelet stimulation would be in individuals at high risk for thrombus formation or reformation including those at risk for advanced coronary artery diseases, and patients undergoing angioplasty procedures (including, for example, balloon, laser, or similar techniques). Inhibition of ADP induced platelet aggregation would be beneficial in patients undergoing surgery with high risk of thrombus formation, including, for example, organ transplantation, coronary bypass surgery, prosthetic valves or vessel transplantation. In addition, the ability of sol-CD39L3 to inhibit platelet activation and recruitment is useful for treatment and or prevention of deep vein thrombosis (DVT), pulmonary embolism (PE), transient ischemic attacks (TIA's) and strokes due to vascular occlusion.

Expression of ecto-apyrase has been observed at the surface of cells developing certain pathologies, including proliferating cancer cells such as human differentiated melanoma and myeloid leukocytes cells (Clifford, E. E., et al., *Am. J. Physiol*. (1997) 42:C973; Dzhandzhugazyan, K. N., et al., *FEBS Lett* (1998) 430:227). Cells infected by pathogens also expressed ecto-apyrase to protect the pathogens from the host immune system. These observations suggested that CD39L3 and/or other CD39 families could be associated with cell-to-cell recognition (Gendron, F. P., et al., *Curr Drug Targets* (2002) 3:229). Therefore using detection methodologies specific to CD39L3 and/or CD39 family members, abnormal cancer cells or infected cells of brain or other tissues may be diagnosed by detecting the abnormal expression level of CD39L3.

Wang and colleagues hypothesized that decrease in ecto-apyrase activity in the brain is the primary cause of partial epilepsy (*Mol. Brain. Res*. (1997) 47:295). Therefore antibodies specific to CD39L3 or CD39 family members are useful for diagnosing abnormal expression of CD39L3 and/or CD39 other families on brain cell surface as an indication of elements of seizure development or maintenance in human temporal lobe epilepsy.

Marcus and his coworkers have proposed thromboregulation mechanism by cell-cell interactions and transcellular metabolism for platelets, neutrophils and endothelial cells (*In: Inflammation*: Basic principles and clinical correlates, 3$^{rd}$ ed., Gallin, J. I., & Snyderman, R. (1999) pp. 77-95). The study showed that the metabolic interchange of biochemical substances generated by platelets and neutrophils can serve mutually to modulate both thrombosis and inflammatory response. Therefore CD39L3 may regulate inflammation through platelet-neutrophil interactions by preventing activation and recruitment of platelets, and by stopping releasing of biochemical metabolites such as hydroxyeicosatetraenaic acids. Therefore CD39L3 and biologically active may indirectly lower inflammation at sites of vascular injury which is especially important for stroke victims.

Mutations in CD39L3 gene may result in loss of the normal function of CD39L3 and undergo related human disease states. Delivering functional CD39L3 gene via gene therapy to appropriate cells can rescue the cells and cure the disease. Alternatively, other human diseases may be caused by abnormally expressed CD39L3 can be treated or cured by negatively regulating CD39L3 expression by antisense therapy or inhibiting CD39L3 function.

CD39L3 or CD39 family members may be used to screen for inhibitors of the enzyme activity. Such inhibition may be competitive, uncompetitive, or noncompetitive inhibitions in the presence of the substrates ATP and ADP. Alternatively an inhibitor can inhibit CD39L3 by binding to allosteric sites. All these inhibitors can be analyzed with soluble CD39L3 or biologically active derivatives in the presence of substrate.

CD39L3 and biologically active derivatives may be used in clinical situations where the hydrolysis of ATP and/or ADP to AMP is clinically beneficent including disease states where ATP and/or ADP concentrations are abnormally high.

In addition, CD39L3 and biologically active derivatives may be administrated in combination with currently available antithrombotic or thrombolytic agents, such as heparin, aspirin, glycoprotein IIb/IIIa antagonist, and recombinant tissue type plasminogen activator (t-PA).

CD39L3 Polypeptides

The molecular cloning and characterization of CD39L3 from human brain is reported by Smith and Kirley (Biochim. Biophys. Acta (1998) 1386:65). CD39L3 is a 529 amino acid protein having high amino acid sequence relatedness to many known ecto-ATPases. Protein analysis suggests that CD39L3 contains a short cytoplasmic region, a potential transmembrane region (near both N-termini and C-termini), and a large extracellular region (localized between the N-terminal and C-terminal transmembrane regions). CD39L3 also maintains a high degree of identity and similarity in the ACR (apyrase conserved regions). As used herein, the term "CD39L3 polypeptides" include CD39L3, homologs of CD39L3, variants, fragments, and derivatives of CD39L3, fusion polypeptides comprising CD39L3, and soluble forms of CD39L3 polypeptides.

CD39L3 is defined as an Ecto-NTPase having both ATPase and ADPase activity in the ratio of 2.75:1. The term "biological activity," as used in herein, includes apyrase enzymatic activity as well as the ex vivo and in vivo activities of CD39L3. Apyrases catalyze the hydrolysis of nucleoside tri- and/or di-phosphates, but a given apyrase may display different relative specificities for either nucleoside triphosphates or nucleoside diphosphates. Biological activity of soluble forms of CD39L3 may be determined, for example, in an ectonucleotidase or apyrase assay (e.g., ATPase or ADPase assays), or in an assay that measures inhibition of platelet aggregation. Exemplary assays are disclosed herein; those skilled in the art will appreciate that other, similar types of assays can be used to measure biological activity.

The key enzymatic activity of CD39L3 resides in the extracellular region; therefore one skilled in the art can effectively engineer a soluble form of CD39L3 by removing, for example, the transmembrane domains. Thus, for applications requiring biological activity, useful CD39L3 polypeptides include soluble forms of CD39L3 such as those having an amino terminus wherein up to 43 amino acids are deleted and a carboxy terminus wherein up to 45 amino acids are deleted; in one embodiment amino acids 1-43 are deleted from the N-terminus and amino acids 485-529 are deleted from the C-terminus and which exhibit CD39L3 biological activity. Alternatively, one skilled in the art can effectively replace the amino acid residues comprising the hydrophobic transmembrane domains with amino acid residues such as serine, glutamic acid, aspartic acid, lysine, arginine, histidine, asparagines, and glutamine so as to generate a soluble polypeptide. Thus permutations and combinations of CD39L3 that will render the protein soluble include but are not limited to deletions of transmembrane domains, substitutions of transmembrane domains, partial deletions or substitutions of transmembrane domains, or polypeptide fusions with amino acid sequences that confer solubility. Such amino acid sequences include soluble polypeptides able to be secreted from the host cells in which they are expressed. A secreted soluble polypeptide can be identified (and distinguished from its non-soluble membrane-bound counterparts) by separating intact cells that express desired polypeptide from the culture medium, e.g., by centrifugation or filtration, and assaying the medium (supernatant or filtrate) for the presence of the desired polypeptide. The presence of the desired polypeptide in the medium indicates that the polypeptide was secreted from the host cells and therefore is a soluble form of the polypeptide. The use of soluble forms of CD39L3 is advantageous for many applications including but not limited to protein purification, biological reactions, therapeutics, and enzymatic reactions.

Among the soluble forms of CD39L3 provided herein are variants (also referred to as analogs) of native CD39L3 polypeptides that retain a biological activity of CD39L3. Such variants include polypeptides that are substantially homologous to native CD39L3, but which have an amino acid composition different from that of a native CD39L3 because of one or more deletions, insertions, or substitutions. When a deletion or insertion strategy is adopted, the potential effect of the deletion or insertion on biological activity must be considered. CD39L3 derivatives of the inventive polypeptides may be constructed by deleting terminal or internal residues or sequences. Additional guidance as to the types of mutations that can be made is provided by a comparison of the sequence of CD39L3 to polypeptides that have similar structures, as well as by performing structural analysis of the inventive polypeptides. Included as variants of CD39L3 polypeptides are those variants that are naturally occurring, such as allelic forms and alternative spliced forms, as well as variants that have been constructed by modifying the amino acid sequence of a CD39L3 polypeptide or the nucleotide sequence of a nucleic acid encoding a CD39L3 polypeptide. It is envisioned that one skilled in the art would be able to identify CD39L3 orthologs or homologues to CD39L3 having for example 70%-100% amino acid identity, preferably 85%-100%, most preferably 95%-100% identical. The invention includes peptides that are at least 70%, 80%, 85%, 90%, 95% or 99% identical to positions 44-484 of SEQ ID NO:20 that have apyrase activity, as well as nucleic acid encoding these peptides. Percent identity, in the case of both polypeptides and nucleic acids, may be determined by visual inspection. It is generally recognized that the biological activity and enzymatic function of CD39L3 are more important with regards to CD39L3 function than overall sequence identity.

Also included within the scope of the invention are fusion polypeptides of CD39L3 and soluble biologically active derivatives that occur at the N-terminal domain, C-terminal domain, or both N-terminal and C-terminal domains. One normally skilled in the art can design fusion polypeptides with CD39L3 and soluble biologically active derivatives of CD39L3 to, for example, simplify protein purification, provide immunological tag, stabilize protein, increase translational efficiency, direct synthesized protein to a particular compartment in the cell, secrete the synthesized protein outside the cell, target the protein to a particular location or cell type, or region of the human or mammalian body, or alter tertiary and quaternary structure of the enzyme.

For example, several strategies are known in the art for generating fusion polypeptide to the N-terminal or C-terminal domains of CD39L3 to aid in the purification of CD39L3 peptides. Such peptides include, for example, poly-His (6×HIS), Glutathione S-transferase (GST), maltose binding protein (MBP), and FLAG® (a convenient binding moiety) peptide. Such sequences may also be used for identification of expressed recombinant protein using antibodies or can be removed from the recombinant protein using specific protease cleavage sites.

As another example, a fusion polypeptide comprising CD39L3 and biologically active derivatives may contain a signal peptide (which is also variously referred to as a signal sequence, signal, leader peptide, leader sequence, or leader) which co-translationally or post-translationally directs transfer of the polypeptide from its site of synthesis to a site inside or outside of the cell membrane or cell wall. It is particularly advantageous to fuse a signal peptide that promotes extracellular secretion to the N-terminus of a soluble CD39L3 polypeptide. In this case, the signal peptide is typically cleaved upon secretion of the soluble CD39L3 from the cell.

In a particularly preferred embodiment, one or more amino acids are added to the N-terminus of a soluble CD39L3 polypeptide in order to improve the expression levels and/or stability of the CD39L3 polypeptide. The one or more amino acids include an Ala residue, fragments derived from the N-terminus of another member of the CD39L3 family (e.g., CD39, CD39L1, CD39L2, CD39L4) or from another polypeptide either naturally-occurring or designed based upon structural predictions, capable of adopting a stable secondary structure.

In a most preferred embodiment, a soluble CD39L3 polypeptide is initially synthesized as a fusion polypeptide comprising: (a) a signal peptide that promotes extracellular secretion of the soluble CD39L3 from the cell, the signal peptide being cleaved upon secretion, (b) one or more amino acids added to the N-terminus of the soluble CD39L3 polypeptide in order to improve expression levels and/or stability, and (c) a fragment of CD39L3 that possesses biological activity. It should also be noted that different expression hosts can process signal peptides differently, thus resulting in alterations and variations of the N-terminal or C-terminal domains. Therefore the present invention also includes variations in the sequence of the N-terminal and C-terminal domains.

It is further envisioned in the present invention that an ideal anti-platelet agent comprising natural or engineered biologically active CD39L3 be capable of hydrolyzing ADP at thrombus while sparing ADP at other natural clot sites. Another particularly useful class of fusion polypeptides includes those that allow localization or concentration of CD39L3 at a site of platelet activation and recruitment. Examples of fusion polypeptides useful in the present invention for targeting the thrombus include but are not limited to; kringle domain of tissue-type plasminogen activator (Runge, M. S., et al., *Circulation* (1989) 79:217-224; Haber, E., et al, *Science* (1989) 243:51-56); fusion of thrombus specific antibody; or addition of protein domain interacting with receptors specific to thrombus; Such fusion polypeptides comprise a moiety that specifically binds activated platelets and CD39L3, and can be prepared using recombinant DNA technology, or by using standard techniques for conjugation of polypeptides. For example, recombinant CD39L3 may also be chemically modified by adding, for example, ligands that specifically bind the thrombus.

In addition to extension by additional amino acid sequence, the CD39L3 peptides of the invention may also be coupled to other agents to form conjugates. For example, the peptide may be coupled to peptidomimetics that target fibrin or other platelet-associated targets, to labels, such as radionuclides, fluorophores, quantum dots, and the like, to substances that effect biological half-life such as polyethylene glycol or fatty acids, or to chelating agents such as EDTA. The peptides may also be coupled to delivery vehicles such as liposomes and nanoparticles or to magnetic beads to aid in separation. Thus, the invention includes the peptides themselves, fusion proteins comprising these peptides, and conjugates of the peptides with a variety of moieties provided such moieties do not destroy the desired enzymatic activity of the CD39L3 peptide.

As another example, modification can be made by one skilled in the art that will alter the protein properties. For example, the primary amino acid sequence of CD39L3 and biologically active derivatives can be modified to, for example, remove or introduce glycosylation sites, remove or add regulatory properties to the enzyme, change the substrate specificity, change the catalytic activity, increase or decrease the pI of the enzyme, improve or reduce the enzyme stability or half-life, reduce the immunogenicity of the protein, alter the charge distribution of the protein, and remove or introduce requirements for cations (such as $Ca^{2+}$) or metal ions.

For example, the present invention further includes soluble CD39L3 polypeptides with or without associated native-pattern glycosylation. CD39L3 expressed in yeast or mammalian expression systems (e.g., HEK293, CHO, COS-7 cells) may be similar to or significantly different from a native CD39L3 polypeptide in molecular weight and glycosylation pattern, depending upon the choice of expression system. Expression of CD39L3 polypeptides in bacterial expression systems, such as *E. coli*, provides non-glycosylated molecules.

All peptide modification to CD39L3 and biologically active derivatives can be combined with appropriate expression systems to generate optimal production and bioactivity of the CD39L3 polypeptide and its biologically active derivatives. Determination of kinetic parameters including ratio of ATPase/ADPase activity of soluble forms of CD39L3 or derivatives may be obtained. Additionally, antibodies specific to CD39L3 or derivatives may also be generated by one skilled in the art.

CD39L3 Nucleic Acids

The present invention relates the full length CD39L3 molecule as well as isolated fragments, oligonucleotides, and truncations maintaining biological activity, for example N-terminal deletions, C-terminal deletions, or deletions at both N and C-termini derived from SEQ ID NO:19 and deduced amino acid sequences SEQ ID NO:20. For example, the nucleotide sequences encoding a soluble form of CD39L3 comprising N-terminal and C-terminal deletions is represented in SEQ ID NO:21 and SEQ ID NO:23 and the deduced amino acid sequences SEQ ID NO:22 and SEQ ID NO:24. The present invention also related to allelic variants of CD39L3 as well as synthetic or mutated genes of CD39L3 that have been modified to change, for example, the expression or activity of the recombinant protein. It is also noted that degeneracy of the nucleic acid code can be considered variations in the nucleotide sequences that encode the same amino acid residues. Therefore, the embodiment of the present invention includes nucleic acid residues that are able to hybridize under moderately stringent conditions. One skilled in the art can determine effective combinations of salt and temperature to constitute a moderately stringent hybridization condition. It is also envisioned that orthologs of CD39L3 are present in other species, for example, dog, sheep, rat, hamster, chicken and pig. Therefore in another embodiment of the present invention relates to CD39L3 nucleic acids that encode polypeptides having at least about 70% to 80% identity, preferably 90% to 95% identity, more preferably 98% to 99% identity to CD39L3 set forth in SEQ ID NO's: 20, 22 24 and 25.

The present invention also relates to recombinant vectors containing a nucleotide sequence encoding SEQ ID NO:20 or fragments thereof. Recombinant vectors include but are not limited to vectors useful for the expression of the open reading frames (ORFs) in *E. coli*, yeast, viral, baculovirus, plants or plant cells, as well as mammalian cells. Suitable expression vectors for expression in a suitable host are known to one skilled in the art and appropriate expression vectors can be obtained from commercial sources or from ATCC. The recombinant vectors useful in the present invention include ORFs comprising CD39L3 or biological active derivatives inserted into vectors useful for the production of protein corresponding to CD39L3. Useful embodiments include, for example, promoter sequences operably linked to the ORF, regulatory sequences, and transcription termination signals.

In addition, the present invention also comprises nucleic acid sequences that have been appropriately modified, for example, by site directed mutagenesis, to remove sequences responsible for N-glycosylation not needed for biological activity. N-glycosylation sites in eukaryotic peptides are characterized by the amino acid sequence Asn-X-Ser/Thr where X is any amino acid except Pro. Modification of glycosylation sites can improve expression in for example yeast or mammalian cell cultures.

The present invention also related to nucleic acid that have been modified to improve the production and solubility of recombinant protein in a suitable host which includes, but is not limited to removing Cysteine residues unnecessary for intramolecular disulfide bond formation. Cysteine residues may be changed by mutagenesis to another amino acid, for example serine, or removed from the sequence without affecting the biological activity or tertiary structure of the recombinant polypeptide.

Other modifications of the nucleic acids may be necessary to improve the stability and accumulation of the recombinant production of protein include but are not limited to mutations altering protease cleavage sites recognized by a suitable expression host. Such modifications can be made that will not adversely affect the biological activity or tertiary structure of the recombinant protein.

Additional modifications can be made to the nucleic acids that result in alterations in enzyme activity, substrate specificity, and/or biological activity. Such modifications may be preconceived based on specific knowledge relating to the protein or may be introduced by a random mutagenesis approach, for example error prone PCR. Additionally, it is also envisioned that one skilled in the art could generate chimeric nucleotide sequence comprising specific domains that can functionally replace stretches of nucleotide sequences that may add new function or improve the specificity or activity of the produced recombinant protein. For example, the nucleotide sequence comprising the catalytic region of CD39L3 may be functionally replaced with a nucleotide sequence from an ortholog or homolog of CD39L3 thereby conferring improved or novel function. Modification resulting in changed biological activity of CD39L3 may be necessary to improve the therapeutic effectiveness of the protein or to minimize potential side effects. Modification of the nucleic acid sequences can also be made that alter potential immunogenic sites that may result in allergic reactions to patients' administered with recombinant CD39L3 protein.

Silent modifications can be made to the nucleic acids that do not alter, substitute or delete the respective amino acid in the recombinant protein. Such modification may be necessary to optimize, for example, the codon usage for a specific recombinant host. The nucleotide sequence of CD39L3 can be modified to replace codons that are considered rare or have a low frequency of appropriate t-RNA molecules to a more suitable codon appropriate for the expression host. Such codon tables are known to exist and are readily available to one skilled in the art. In addition, silent modification can be made to the nucleic acid that minimizes secondary structure loops at the level of mRNA that may be deleterious to recombinant protein expression.

Expression Systems Useful for Production of CD39L3

The present invention also provides for recombinant cloning and expression vectors useful for the production of biologically active CD39L3. Such expression plasmids may be used to prepare recombinant CD39L3 polypeptides encoded by the nucleic acids in a suitable host organism. Suitable host organisms for the production of CD39L3 and functional derivatives include but are not limited to bacteria, yeast, insect cells, mammalian cells, plants and plant cells. In addition, cell free systems may also be employed for the production of recombinant proteins. One skilled in the art can readily prepare plasmids suitable for the expression of recombinant CD39L3 in the suitable host organism. Appropriate cloning and expression vectors are readily available to one skilled in the art and can be obtained from commercial sources or from the ATCC.

The recombinant protein can be produced in the within the host cell or secreted into the culture medium depending on the nature of the vector system used for the production of the recombinant protein. Generally plasmids useful for the expression of the recombinant CD39L3 comprise necessary operable linked regulatory elements such as a promoter sequence (including operators, enhancers, silencers, ribosomal binding sites), transcriptional enhancing sequences, translational fusions to signal peptides (native or heterologous) or peptide sequences useful for the purification of recombinant protein (for example His Tag, FLAG® (a convenient binding moiety), MBP, GST), transcription termination signals and poly adenylation signals (if necessary).

It may also be necessary for the recombinant plasmid to replicate in the host cell. This requires the use of an origin of replication suitable for the host organism. Alternatively, the recombinant expression plasmid may be stably integrated into the host's chromosome. This may require homologous recombination or random integration into the host chromosomes. Both instances require the use of an appropriate selection mechanism to distinguish transformed host cells from non-transformed host cells. Useful selection schemes include the use of, for example, antibiotics (for example, G418, Zeocin® (a glycopeptide antibiotic of the bleomycin family), kanamycin, tetracycline, gentamycin, spectinomycin, ampicillin), complementation of an auxotroph (for example Trp-, DHFR-), and scorable markers (for example β-glucoronidase, β-galactosidase, GFP).

Expression systems useful in the present invention include yeast systems particularly suitable for expression of human secretory proteins. For example the yeast expression system based on *Kluyveromyces lactis* has been particularly successful for the recombinant production of human secretory proteins (Fleer, R., et al., *Gene* (1991) 107:285-295; Fleer, R., et al., *Biotechnology* (1991) 9:968-997). Plasmid vectors particularly useful for the transformation and expression of protein in recombinant *K. lactis* have been descried (Chen, X-J., *Gene* (1996) 172:131-136). Other yeast expression systems based on *Saccharomyces cerevisiae* or *Pichia pastoris* or *Pichia methanolica* may also be useful for the recombinant production of CD39L3. Expression plasmid suitable for the expression of CD39L3 in *S. cerevisiae, P. pastoris*, or *P. methanolica* may be obtained from a commercial source or ATCC. Plasmids described above may also be modified by one skilled in the art to optimize, for example, promoter sequences and or secretion signals optimal for the host organism and recombinant production of CD39L3. Established methods are also available to one skilled in the art for introducing recombinant plasmid into the yeast strains.

Expression of recombinant CD39L3 in mammalian cell culture is also a preferred embodiment of the present invention. There are a wide variety of mammalian cell lines available to one skilled in the art. The most widely used and most successful mammalian expression system is based on a dhfr- (dihydrofolate reductase) Chinese hamster ovary (CHO) cell line along with a suitable expression plasmid containing the dhfr gene and suitable promoter sequence. The cells may be transfected for transient expression or stable expression of the protein of interest. Other factors for the production of foreign protein in mammalian cells including regulatory considerations have been reviewed (Bendig, M., *Genetic Engineering* (1988) 7:91-127). A particularly useful mammalian expression system for production recombinant CD39L3 is based on the EF-1α promoter (Mizushima, S and Nagata *Nucleic Acids Res* (1990) 18:5322) and Human embryonic kidney (EK) 293T cell line (Chen, P., et al., *Protein Expression and Purification* (2002) 24:481-488). Variants of the commercially available CHO and 293T cells lines and their suitable growth and expression media may be used to further improve protein production yields. Variants of commercially available expression vectors including different promoters, secretion signals, transcription enhancers, etc., may also be used to improve protein production yields.

Another expression system useful in the present invention includes expression in *E. coli*. There are several expression systems known to one skilled in the art for production of recombinant proteins in *E. coli*. Expression of mammalian protein in *E. coli* has not been particularly useful due to the fact that many mammalian proteins are post translationally modified by glycosylation or may contain intra or inter di-sulfide molecular bonds. Particular *E. coli* expression plasmid useful in the present invention may include, for example, fusions with signal peptides to target the protein to the periplasmic space. Additionally, *E. coli* host strains that contain mutations in both the thioredoxin reductase (trxB) and glutathione reductase (gor) genes greatly enhance disulfide bond formation in the cytoplasm (Prinz, W. A., et al., *J. Biol. Chem.* (1997) 272:15661-15667). The addition of thioredoxin fused to the N-terminus or C-terminus of CD39L3 may also aid in the production of soluble protein in *E. coli* cells. (LaVallie, E. R., et al., *Bio/Technology* (1993) 11:187-193).

Other expression systems known in the art may also be employed for the production of active CD39L3 and include but are not limited to baculovirus expression (Luckow, V., *Curr Opin Biotechnol* (1993) 5:564-572) or the production of recombinant CD39L3 in a plant leaf or seeds, for example corn seeds.

Purification of biologically active CD39L3 from may be purified from the recombinant expression system using techniques known to one normally skilled in the art. Expression of the CD39L3 protein can either be intracellular or secreted in the media fraction. Secretion of CD39L3 into the media simplifies protein purification and is the preferred embodiment in the present invention. Expression of intracellular CD39L3 requires disruption of the cell pellets by any convenient method including freeze-thaw, mechanical disruption, sonication, or use of detergents or cell lysing enzymes or agents. Following disruption or concentration of secreted protein, purification of CD39L3 can be accomplished by a number of methods know to one skilled in the art. For example, commercially available affinity chromatography may be used to purify recombinant CD39L3 fusions with affinity tags such as: 6×HIS, FLAG® (a convenient binding moiety), GST, or MBP. In addition, antibodies specific to CD39L3 may be used for affinity purification. In addition, matrices chemically modified with a ligand having strong affinity to CD39L3 as a substrate mimic may also be used for affinity purification. CD39L3 may also be purified with the use of an affinity tag or antibodies following conventional protein purification methods know to one skilled in the art.

The desired degree of purity of CD39L3 must also be taken into consideration. For application involving administration of CD39L9 in vivo, highly purified CD39L3 is desirable. Most preferable purification of CD39L3 should result in no detectable band corresponding to other (non-CD39L3) polypeptides on a silver stained SDS-Page gel. It should also be noted that depending on the recombinant expression system used other bands corresponding to CD39L3 may be visible. This may be due to alterations in protein glycosylation, internal ribosome initiation, post-translation modification and the like.

Methods for In Vitro and In Vivo Validation of CD39L3 Efficacy

Biochemical function of CD39L3 or derivatives may be assessed by numerous methods available to one skilled in the art. For example, ATPase and ADPase enzyme activities of purified soluble CD39L3 can be determined at 37° C. in a 1 ml solution containing 8 mM $CaCl_2$, 200 µM substrate (ATP for ATPase or ADP for ADPase), 50 mM imidazole, and 50 mM Tris, pH7.5 (Picher, et al., *Biochem. Pharmacol.* (1988) 51:1453). The reaction can be stopped and inorganic phosphate released can be measured by addition of 0.25 ml of malachite green reagent (Baykov, et al., *Anal. Biochem.* (1988) 171:266). Based on the spectrophotometric analysis at 630 nm, one unit of ATPase (or ADPase) corresponds to release of 1 µmole of inorganic phosphate/min at 37° C. Key kinetic constants for the enzyme such as $K_m$ and $k_{cat}$ may be obtained by fitting data into, for example, a Michaelis-Menten equation. Other assays useful for monitoring biochemical function include, but are not limited to, a radiometric assay, a HPLC assay both described by Gayle III, et al. (*J. Clin Invest.* (1998) 101:1851-1859) or a radio-TLC assay described by Marcus, A. J., et al. (*J. Clin Invest.* (1991) 88:1690-1696).

Biological function of CD39L3 or derivatives may be assessed by ex vivo methods as well as in vivo methods. Ex vivo methods useful for monitoring the biological function of CD39L3 and derivatives include, for example, platelet aggregation assays (Pinsky, D. J., et al., *J. Clin Invest.* (2002) 109:1031-1040; Ozaki, Y, *Sysmex J. Int* (1998) 8:15-22).

In vivo methods useful for assessing the biological functions of CD39L3 and derivatives include, but are not limited to, murine stroke model measuring bleeding time, infarction volume, blood flow, neurological deficit, intracerebral hemorrhage, and mortality (Pinsky, D. J., et al., *J. Clin Invest.*

(2002) 109:1031-1040; Choudhri, T. F., et al., *J. Exp. Med.* (1999) 90:91-99), murine lung ischemia/reperfusion model (Fujita, T., et al., *Nature Med.* (2001) 7:598-604), baboon model of reperfused stroke (Huang, J., et al., *Stroke* (2000) 31:3054-3063), cd39$^{-/-}$ mice (Pinsky, D. J., et al., *J. Clin Invest.* (2002) 109:1031-1040) and Yorkshire-Hampshire Pig model of thrombosis (Maliszewski, C. R., et al., PCT WO 00/23094 (2000)). Other methods may be known to one skilled in the art for assessing the biological function of CD39L3 and derivatives as a thromboregulator.

Therapeutic Compositions of CD39L3

The present invention provides compositions comprising a biologically effective amount of CD39L3 polypeptide or biologically active derivative in a pharmaceutically acceptable dosage. Therapeutic composition of CD39L3 or biologically active derivative may be administered clinically to a patient before symptoms, during symptoms, or after symptoms. After symptom administration of CD39L3 or biologically active derivates preferably occurs at about 6 hours following symptom, more preferably at about 3 hours following symptoms. Administration of CD39L3 or biologically active derivatives to achieve therapeutic effect may be given by, for example, bolus injection, continuous infusion, sustained release, or other pharmaceutically acceptable techniques. Certain clinical situations may require administration of CD39L3 or biologically active derivatives as a single effective dose, or may be administered daily for up to a week or a much as a month or more. Ideally CD39L3 will be administered to patients in a pharmaceutically acceptable form containing physiologically acceptable carriers, excipients or diluents. Such diluents and excipients may be comprised of neutral buffered saline solution, antioxidants (for example ascorbic acid), low molecular weight polypeptides (for example polypeptides $\leq 10$ amino acids) amino acids, carbohydrates (for example, glucose, dextrose, sucrose, or dextrans), chelating agents such as EDTA, stabilizers (such as glutathione). Additionally, cosubstrates for the CD39L3 or biologically active derivatives, for example, calcium ($Ca^{2+}$) may be administered at time of dosage for maximal activity of the enzyme. Such carriers and diluents will be nontoxic to the patient at recommended dosages and concentrations. It is also envisioned in the present invention that CD39L3 or biologically active derivatives may be administer with other agents that synergistically enhance the benefit of CD39L3 or biologically active derivatives alone. For example, it is envisioned that administration of aspirin with CD39L3 or biologically active derivative may have added benefits. It is also envisioned that administration of CD39L3 or biologically active derivatives may lower the effective dosage of drugs like tissue plasminogen activator (Activase® and TNKase™).

Certain clinical situations may require the slow and prolonged release of biologically active CD39L3 or biological derivatives. Such situations may require the sequestrations of CD39L3 or biological derivatives in, for example, hydrogel or other pharmaceutically acceptable polymerizable gels. Additionally, a polyethylene glycol (PEG) can be added to prolong the blood half-life to increase efficacy of a soluble CD39L3. In the case where CD39L3 is used as a preventative medication, this may allow for single-bolus dose administration to maintain protective effects of CD39L3 for longer periods. Other protein modifications to alter protein half-life include, for example, albumin conjugation, IgG fusion molecules and altering of the proteins glycosylation pattern.

Dosage requirements of CD39L3 or biologically active derivatives may vary significantly depending on age, race, weight, height, gender, duration of treatment, methods of administration, biological activity of CD39L3, and severity of condition or other clinical variables. Effective dosages may be determined by a skilled physician or other skilled medical personnel.

The clinical and biological effectiveness of the administered CD39L3 or biological derivative can be readily evaluated at given time intervals after administration. For example, administration of CD39L3 or biological derivatives should promote longer bleeding times in the setting where platelet count remains unchanged. Additionally, direct measurement of blood samples for enzyme activity of CD39L3 or biological derivative will also indicate presence of the molecule in the circulating blood. Based on precise sampling of blood samples coupled with methods known in the art for assessing biochemical function of CD39L3 the half life of the protein can be estimated. Additional clinically relevant assays for the presence of biologically active CD39L3 or biologically active derivative may also be envisioned.

The following examples are intended to illustrate but not to limit the invention.

EXAMPLE 1

Identification of CD39L3 as an Isozyme of CD39

CD39 has been established as a key thromboregulator and essential for regulating normal blood flow. However, northern blot analysis on multiple human tissues demonstrated negligible expression of CD39 in brain. The brain is a blood vessel rich organ that requires thromboregulation. Since CD39 is a key thromboregulator and it is not expressed in sufficient quantities in human brain tissue an isoenzyme of CD39 should likely be present. Based upon the expression patterns of the CD39 family in human brain tissue, CD39L3 was highly expressed. Protein informatics analysis for CD39 and CD39L3 demonstrated the following: (1) ATPase and ADPase activities were similar in terms of initial velocities (Smith and Kirley, *Biochemica et Biophysica Acta*, (1998) 1386:65-78; Gayle, R. B. III, et al., *J. Clin Invest.* (1998) 101:1851-1859.) (2) Protein hydrophobicity profiles of CD39 and CD39L3 were similar (Chadwick and Frischauf, *Genomics* (1998) 50:357-367). (3) Protein physicochemical properties such as number of amino acid residues, pI, and percent composition of each amino acid for CD39 and CD39L3 were similar (FIG. 2). (4) Pairwise comparison of CD39L3 and CD39 (FIG. 3) demonstrated residues in the known apyrase conserved regions (ACRs) were nearly identical, although the overall protein identity was about 30% (Thompson, J. D., et al., *Nucleic Acids Res* (1994) 22:4673-4680). (5) Swiss-Prot analysis indicated that CD39L3, like CD39, contains potential transmembrane domains at both the N- and C-termini (Bairoch, A. & Apweiler, R., *Nucleic Acids Res* (2000) 28:45-48). (6) Ten cysteine residues in the extracellular region of CD39 are structurally conserved in CD39L3 (FIG. 3). (7) Key residues involved in adenine binding, for example tyrosine, cysteine, phenylalanine and serine, are conserved in both proteins (FIG. 3). (8) The genomic DNA sequence containing ten exons are perfectly aligned with CD39 and CD39L3. (9) Like CD39 the ACRs of CD39L3 are in one of the exons (FIG. 3). Based on the protein informatics evidence, it strongly suggests that CD39L3 is the only known isoenzyme of CD39 and most likely is the dominant thromboregulator in human brain tissue.

EXAMPLE 2

Cloning of CD39L3

CD39L3 has been determined to be an isozyme of CD39 that is preferable expressed in human brain tissue. Chadwick and Frischauf (*Genomics* (1998) 50:357-367) have studied the tissue distribution of several CD39 family members including CD39L3. Based on their observations it is clear that CD39L3 is predominately expressed in Human brain and pancreas tissues and represent preferred source material for cloning CD39L3. Other tissue sources useful for cloning CD39L3 include but are not limited to placenta, spleen, prostate, ovary, small intestine and colon.

Cloning of CD39L3 can be accomplished by numerous methods available to one skilled in the art. For example, total RNA or poly-A RNA can be purified from source tissues mentioned supra and used as a template for gene specific RT-PCR. Additionally, pre-made cDNA libraries can be purchased from commercial sources and PCR can be employed to amplify the CD39L3 cDNA directly. Still further, synthetic oligos can be constructed to create a synthetic gene for CD39L3 based on sequence information available for CD39L3 (Genbank: gi|4557425). Additionally, full length cDNA clones can be obtained from, for example, the IMAGE clone consortium.

Figure 4:
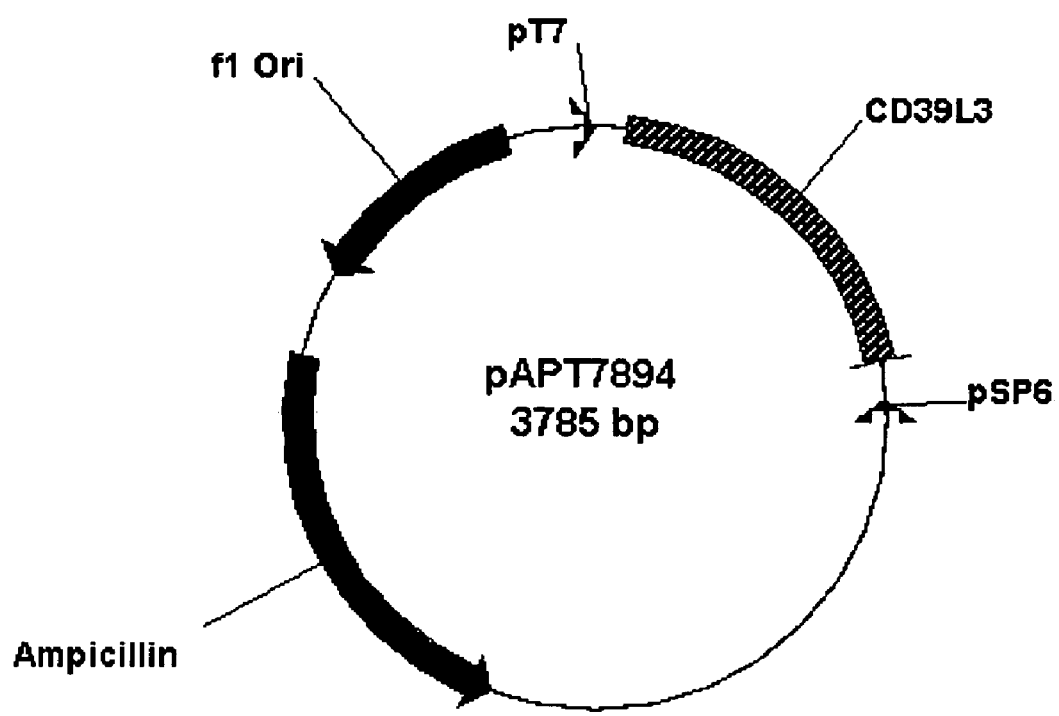
FIG. 4 is a diagram of plasmid pAPT 7894 comprising nucleotides 1 to 640 of CD39L3 (SEQ. ID. NO: 19) cloned into pGEM-T easy.
Figure 5:
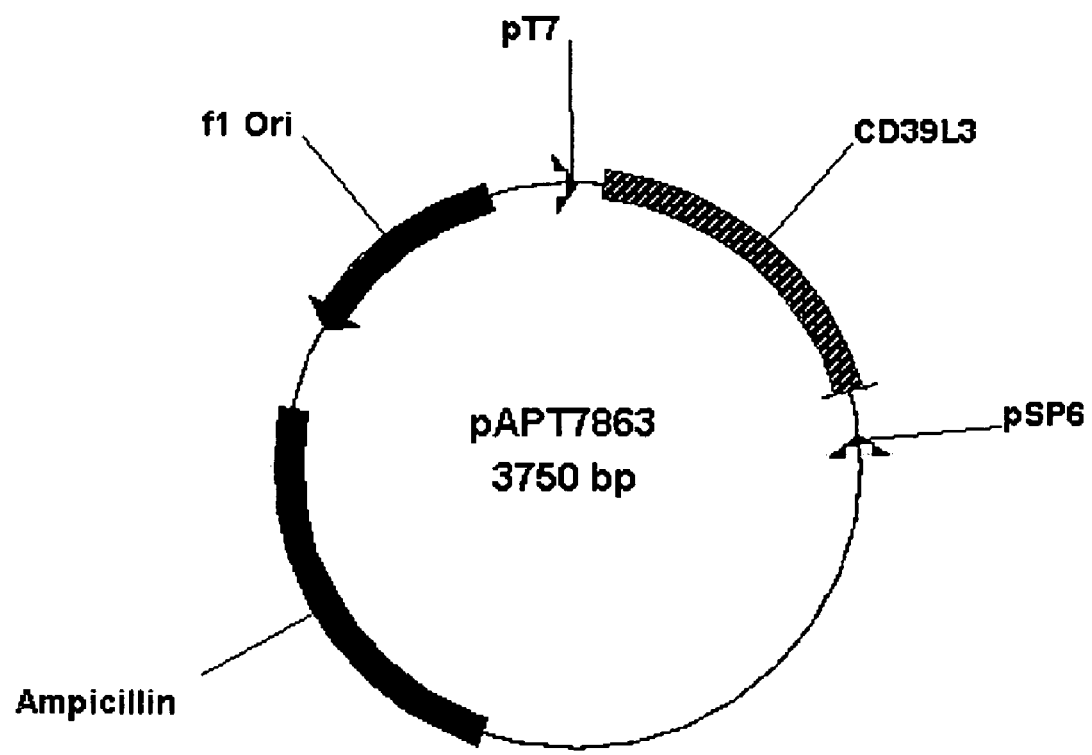
FIG. 5 is a diagram of plasmid pAPT 7863 comprising nucleotides 635 to 1218 of CD39L3 (SEQ. ID. NO: 19) cloned into pGEM-T easy.
Figure 6:
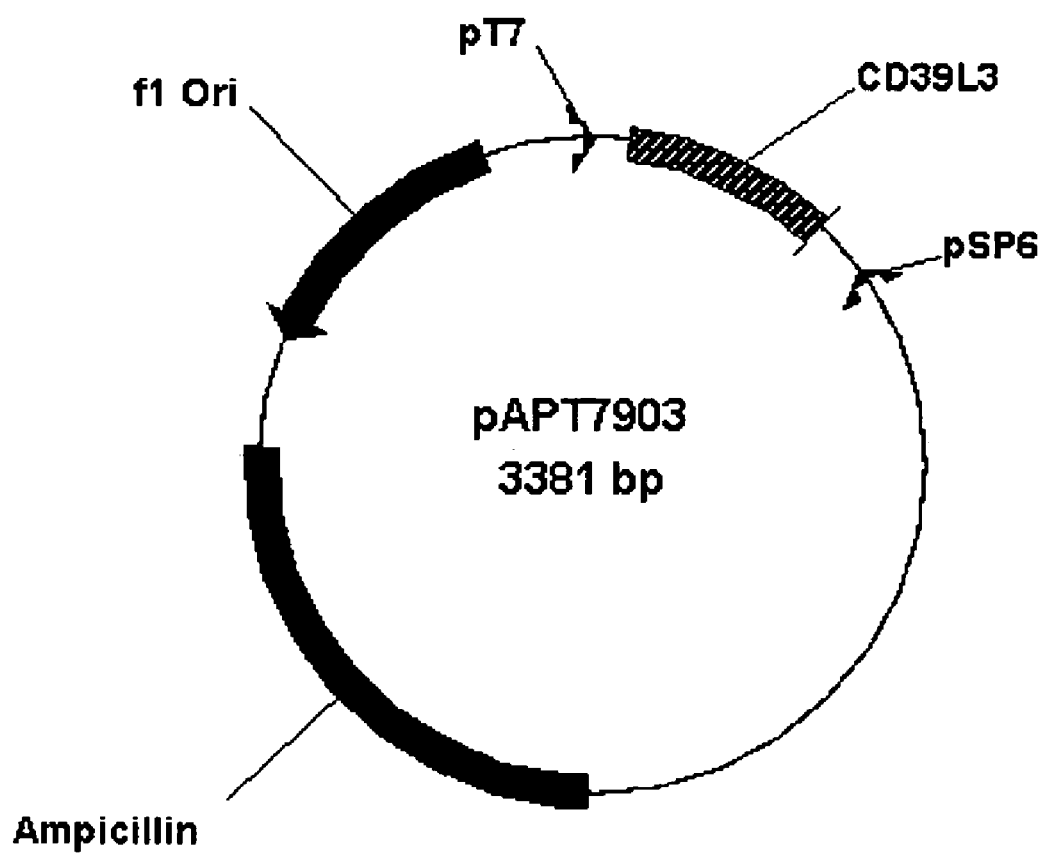
FIG. 6 is a diagram of plasmid pAPT 7903 comprising nucleotides 1240-1590 of CD39L3 (SEQ. ID. NO: 19) cloned into pGEM-T easy.
Figure 7:
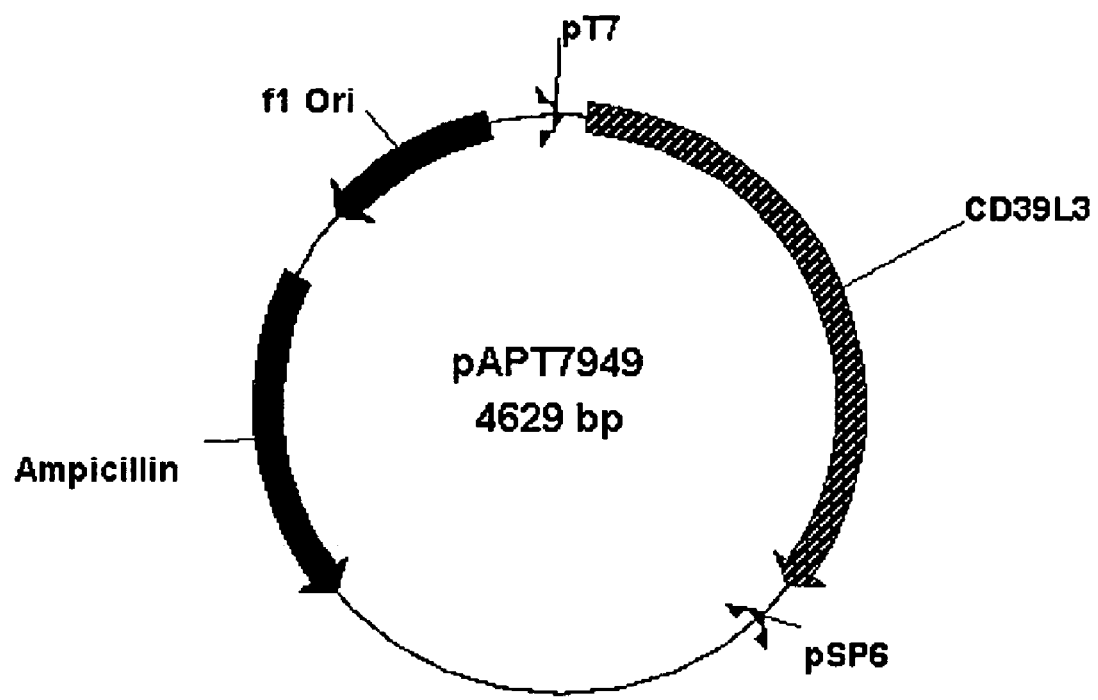
FIG. 7 is a diagram of plasmid pAPT7949 comprising the full length CD39L3 (SEQID 19) gene cloned into pGEM-T easy.

CD39L3 was cloned from the Large-Insert Human Brain cDNA Library (Clontech Palo Alto, Calif. Cat # HL5500u, Lot #1070483) by PCR using gene specific primers. An NcoI site was introduced at the translations start site for CD39L3 for convenient cloning into expression plasmids. CD39L3 was cloned by combining 5 ul of library extract, 1 ul of 5' primer (100 ng), 1 ul of 3' primer (100 ng) and 50 ul PCR Supermix High Fidelity (Invitrogen, Carlsbad, Calif.). 30 cycles of PCR under the following conditions 94C-30 sec, 55C-30 sec, 72C-1 min were performed The full length CD39L3 clone was obtained in three separate PCR reactions. The 5' portion of the gene was amplified with the primer CD39L3 5'FL (SEQ ID NO:1) and primer L3-8 (SEQ ID NO:12). The middle portion of the gene was amplified with primer L3-3 (SEQ ID NO:7) and CD39L3 3' (SEQ ID NO:4) and the 3' end of the gene was amplified with primer L3-5 (SEQ ID NO:9) and CD39L3 3' FL (SEQ ID NO:3). Amplified products were cloned into pGEM-T Easy (Promega, Madison, Wis.) and sequenced resulting in pAPT7894 (FIG. 4), pAPT7863 (FIG. 5), and pAPT7903 (FIG. 6) respectively. The full length cDNA was constructed using convenient restrictions sites located within the coding region, PCR primers and pGEM-T Easy resulting in the production of plasmid pAPT7949 (FIG. 7). The primers used for sequencing the CD39L3 gene are designated L3-1 through L3-10 (SEQ ID NO's:5-14). The sequence of the cloned full length CD39L3 is shown as SEQ ID NO:19 and the deduced amino acid sequence is shown as SEQ ID NO:20. Based on the sequence results obtained, amino acid 496 was changed from valine to alanine. Site directed mutagenesis may be used to change the amino acid back to valine.

EXAMPLE 3

Design and Cloning of a Soluble Form of CD39L3

The protein sequence of CD39L3 was analyzed by Swiss-Prot (Bairoch, A. & Apweiler, R., *Nucleic Acids Res* (2000) 28:45-48). The analysis indicated that CD39L3 has a transmembrane domain at both the N- and C-termini (FIG. 1), for example 23 to 43 in N-terminus and 486 to 506 in C-terminus. Also seven potential N-glycosylation sites are identified. Based on the analysis, a soluble form of CD39L3 was designed by removing the N-terminal 44 amino acids and the C-terminal 43 amino acids.

Figure 8:
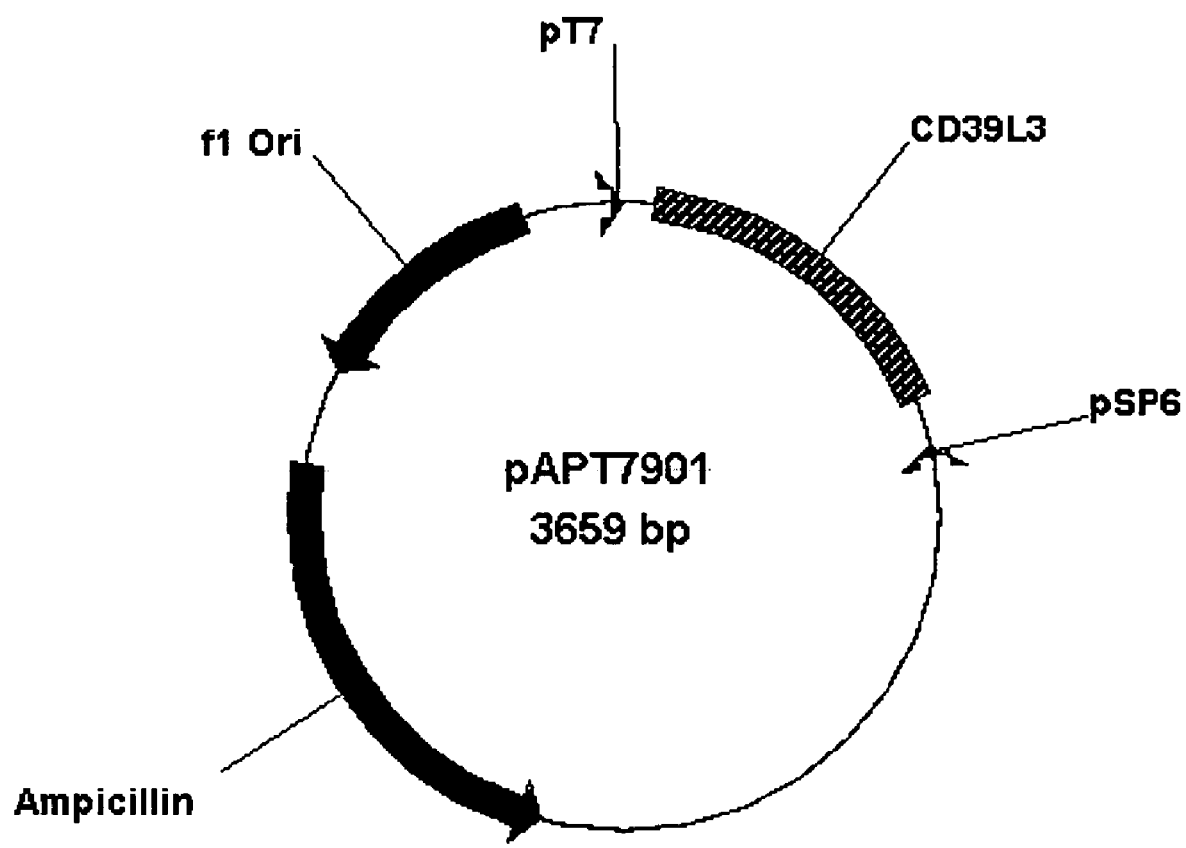
FIG. 8 is a diagram of plasmid pAPT7901 comprising nucleotides 1 to 634 of sol-CD39L3 (SEQ. ID. NO: 21) cloned into pGEM-T easy.
Figure 9:
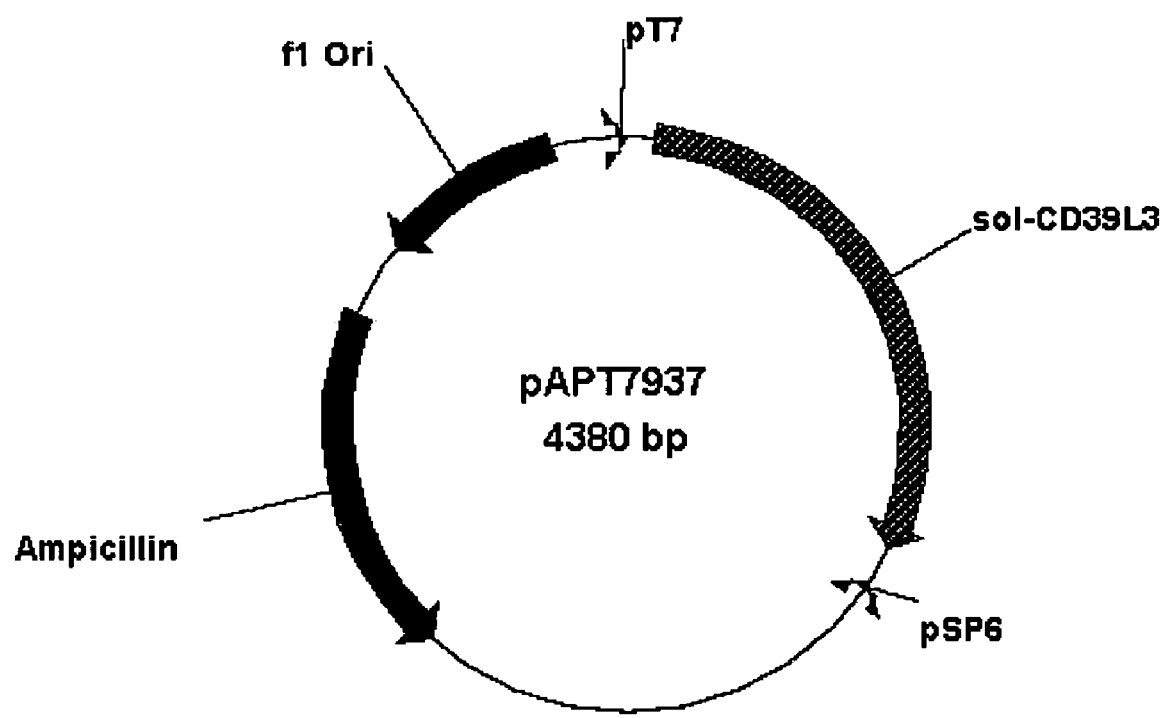
FIG. 9 is a diagram of plasmid pAPT7937 comprising the sol-CD39L3 gene (SEQ. ID. NO: 21) cloned into pGEM-T easy.

The soluble form of CD39L3 was obtained by PCR using the primers CD39L3 5' (SEQ ID NO:2) and L3-8 (SEQ ID NO:12). The PCR product was sequenced and subcloned in pGEM-T Easy resulting in plasmid pAPT 7901 (FIG. 8). The complete truncated CD39L3 was obtained by operably combining the coding regions of CD39L3 from plasmids pAPT7901 (digested Not I/SnaBI) and pAPT7863 (digested SnaBI/NotI) resulting in plasmid pAPT7937 (FIG. 9). The nucleotide sequence of the soluble form of CD39L3 is designated as SEQ ID NO:21 and the protein sequence is designated as SEQ ID NO:22.

EXAMPLE 4

Expression of Soluble Form of CD39L3

Figure 10:
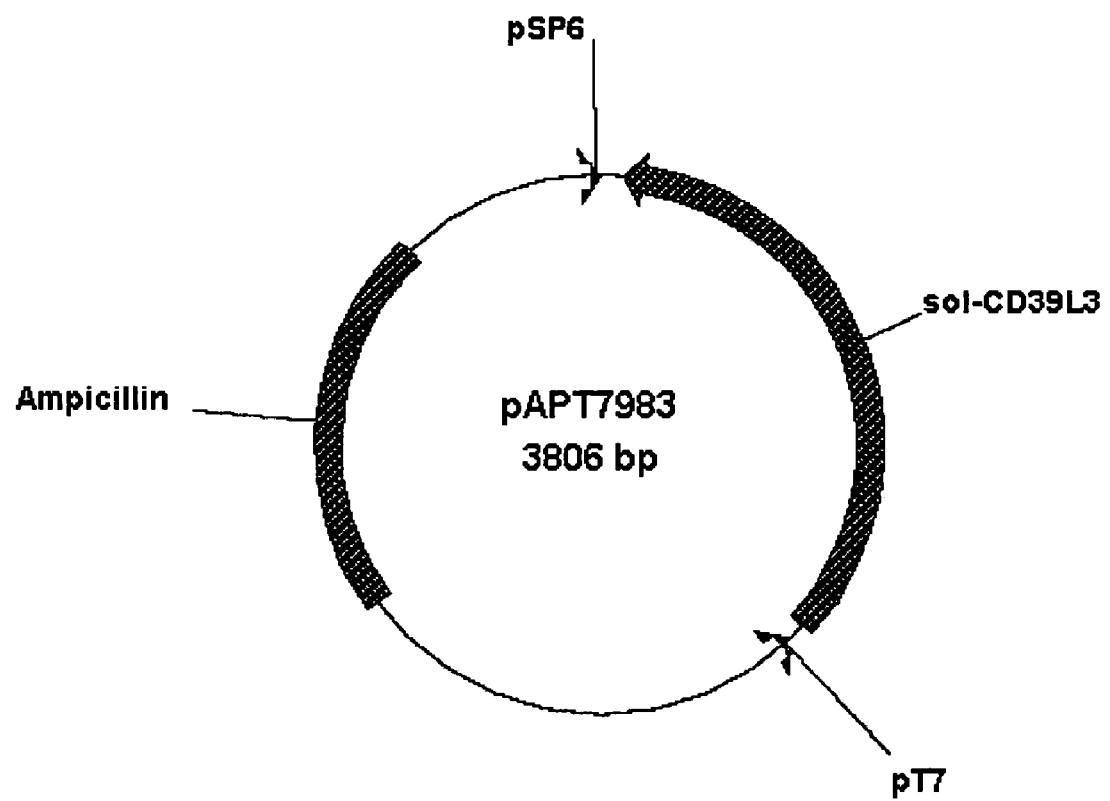
FIG. 10 is a diagram of plasmid pAPT7983 comprising the sol-CD39L3 gene (SEQ. ID. NO: 23) cloned into pSP72.

In order to facilitate cloning of CD39L3 into vectors suitable for expression in mammalian cells (for example, CHO, COS, HEK293), the soluble form of CD39L3 was modified by PCR to introduce a SmaI restriction site in frame with the ATG of soluble CD39L3 using PCR primers L3-Sma5' (SEQ ID NO:15) and L3-Sma3' (SEQ ID NO:16). The resulting PCR product was cloned into the SmaI site of pSP72 (Promega, Madison, Wis.) and the sequence was reconfirmed resulting in plasmid pAPT7983 (FIG. 10). The nucleotide sequence of the sol-CD39L3 is designated SEQ ID NO:23 and the deduced amino acid sequence designated SEQ ID NO:24.

Figure 12:
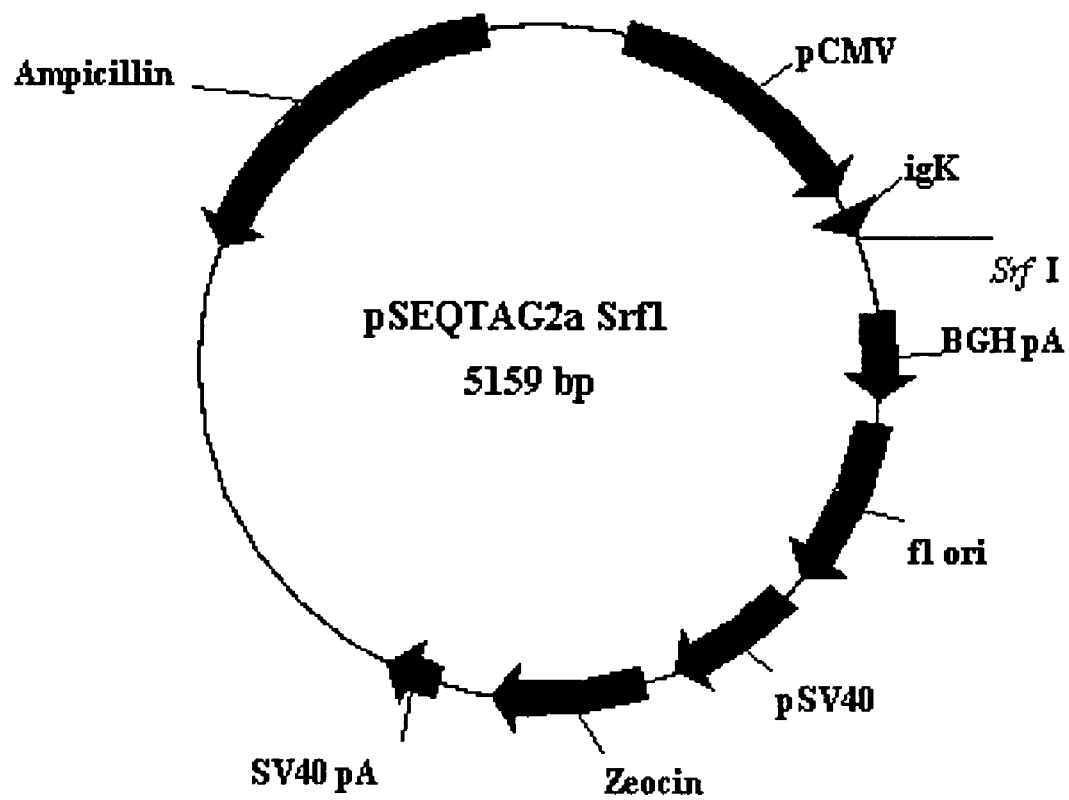
FIG. 12 is a diagram of the plasmid pSEQTAG2a Srfi generated by the site directed mutagenesis of pSEQTAG2a to introduce a Srf I restriction site in frame with the IgK leader sequence.
Figure 13:
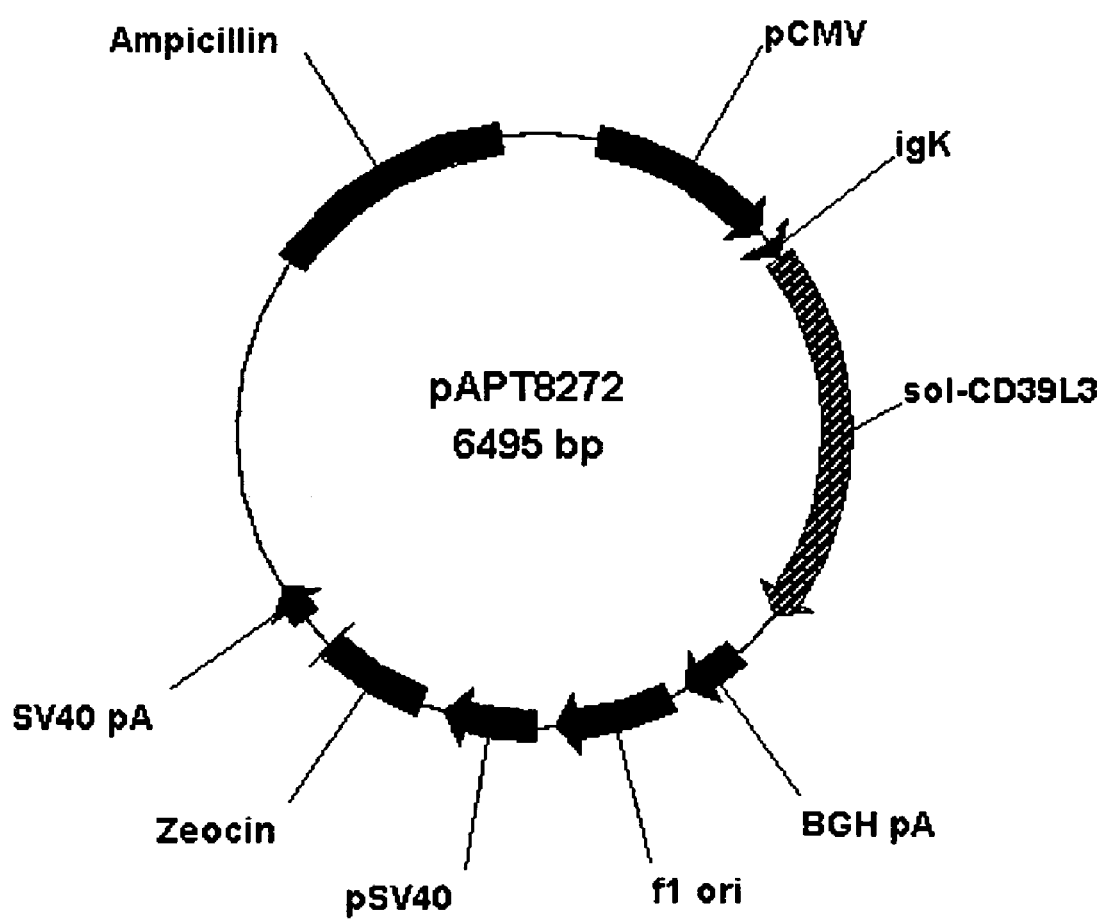
FIG. 13 is a diagram of the sol-CD39L3 mammalian expression plasmid. Sol-CD39L3 (SEQ ID NO:23) is translationally fused to the IgK leader sequence and expression driven by the CMV promoter when transfected into suitable mammalian cells.

In addition, pSEQTAG2A (Invitrogen, Carlsbad Calif.) was also modified by site directed mutagenesis (Quick Change, Stratagene, Carlsbad, Calif.) to introduce a Srf I restriction site in frame with the Igκ leader sequence (FIG. 11) using mutagenesis primers Seqtag2-srfA (SEQ ID NO:17) and Seqtag2-srfB (SEQ ID NO:18). The SmaI fragment containing soluble CD39L3 from pAPT7983 was translationally fused to the SrfI site in plasmid pSEQTAG2a SrfI (FIG. 12) resulting in plasmid pAPT8272 (FIG. 13). Proper post translation processing of the secretory Igκ leader sequence will result in the fusion of four additional amino acids (D-A-P-G) to the N-terminus of sol-CD39L3 (SEQ ID NO:25).

EXAMPLE 5

Transient Transfection and Partial Purification of solCD39L3 in HEK293T Cells pAPT8272 (FIG. 13) containing solCD39L3 cDNA (SEQ ID NO:23) was transfected into 293T cell lines (GenHunter, Nashville, Tenn.) in four 100 mm dishes using transfectant FuGene 6 (Roche) according to manufacturer's recommendations. Transfected cells were grown in DMEM medium, supplemented with 1% BCS, 1% MEM non-essential amino acids, 1% penicillin-streptomycin and 2 mM L-glutamine. After 3 days growth, the conditioned medium (CM) was collected and the cell debris was removed by centrifugation. All the proteins in CM were harvested by centrifugation after 65% ammonium sulfate precipitation. The pellet was dissolved in 2.5 ml of 20 mM Tris-HCl, pH7.4, and desalted through EconoPac 10DG desalting column (BioRad, Hercules, Calif.). Total 4 ml of desalted CM was loaded on a DEAE column and washed with 10 ml of 20 mM Tris-HCl (pH7.4) and 10 ml of 50 mM NaCl in the Tris buffer. SolCD30L3 was eluted with 10 ml of 300 mM NaCl in the Tris buffer. For platelet aggregation study, the buffer was exchanged by 1× Tris buffered saline (Sigma, St. Louis, Mo.).

EXAMPLE 6

Activity of Soluble Form of CD39L3

Figure 14:
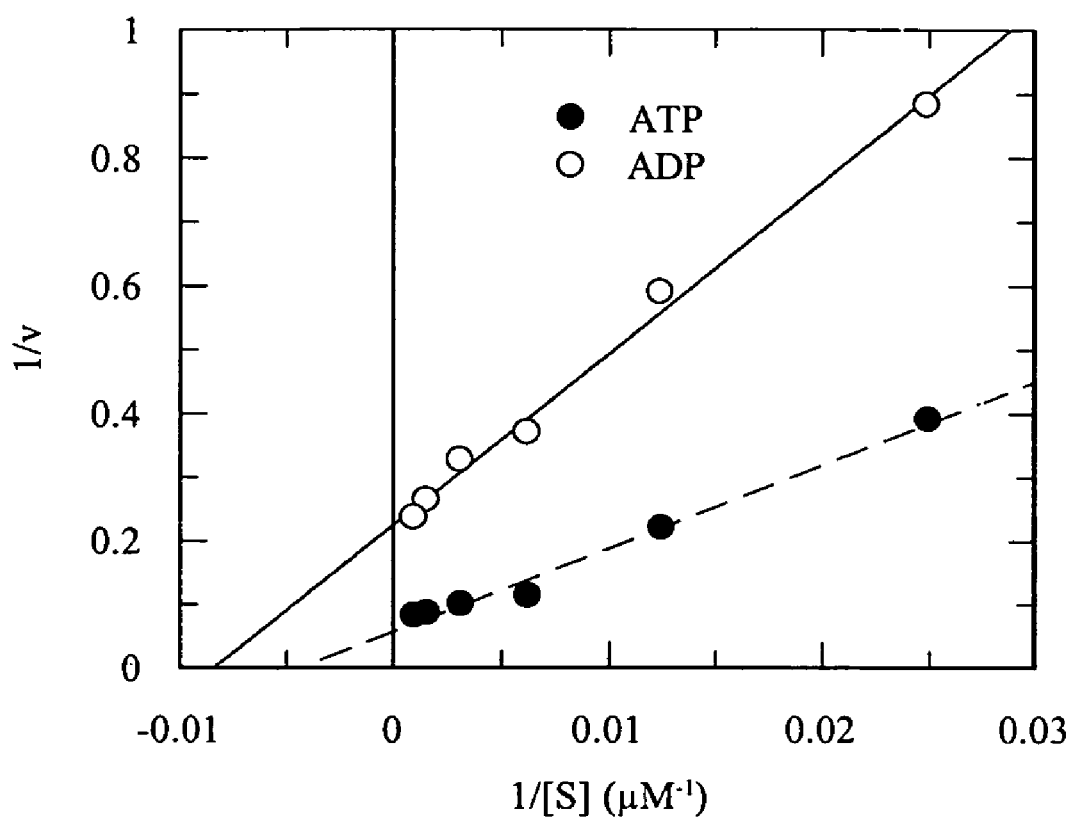
FIG. 14 is the Lineweaver-Burk plot of ADPase and ATPase activities of partially purified soluble CD39L3.

The ADPase and ATPase activities of soluble CD39L3 were estimated by ADP and ATP hydrolysis assays using malachite green (Baykov, et al., *Anal. Biochem.* (1988) 171:266-270). Enzymatic analysis was initiated by the addition of 5 µl of the partially purified solCD39L3 to 495 µl of a mixture containing 50 mM Tris-HCl (pH7.4), 8 mM CaCl$_2$, and various concentrations of ADP or ATP. Following 30 minute incubation at 37° C., 50 µl of the reaction solution was mixed with 900 µl of 50 mM Tris-HCl (pH7.4) and 50 µl of the malachite working solution. The inorganic phosphate released from the ADP or ATP reacts with the malachite working solution, resulting in a green color. Since the enzymatic activity of solCD39L3 is proportional to the amount of the released inorganic phosphate, solCD39L3 activity can be measured by monitoring the absorbance at 630 nm using an Agilent 8453 UV-Visible spectrophotometer (Agilent, Palo Alto, Calif.). The kinetics of the enzymatic reaction was determined by measuring the time course of the color development at a wavelength of 630 nm. Initial rates of ADP hydrolysis by the recombinant soluble CD39 were determined and kinetic constants were derived. The $K_m$ and $V_{max}$ of the recombinant solCD39L3 for ADP were determined to be 134.09 µM and 4.67, respectively; for ATP a $K_m$ of 135.93 µM and $V^{max}$ of 14.11 were estimated (FIG. 14, FIG. 15). These results show CD39 and CD39L3 have comparably catalytic efficiency for ADP with a ration of $V_{max}/K_m$ for ADP of 0.0315 and 0.0348 respectively. In addition the ratio of $V_{max}/K_m$ for ADP to ATP is calculated to be 1:3 that is close to the calculated ADPase:ATPase of CD39, 1:2.2; further supporting both enzymes are isozymes. Also when Radio-TLC assays were employed for ADPase and ATPase activities of solCD39 and solCD39L3 (Gayle III et al. (1998) *J. Clinical Investigation* 101:1851-1859), the ratio of ADPase:ATPase was 1:1.58 and 1:1.83 for solCD39 and solCD39L3, respectively. With two independent kinetic assays we concluded that CD39L3 is an isozyme of CD39.

EXAMPLE 7

Platelet Aggregation Studies

Figure 16:
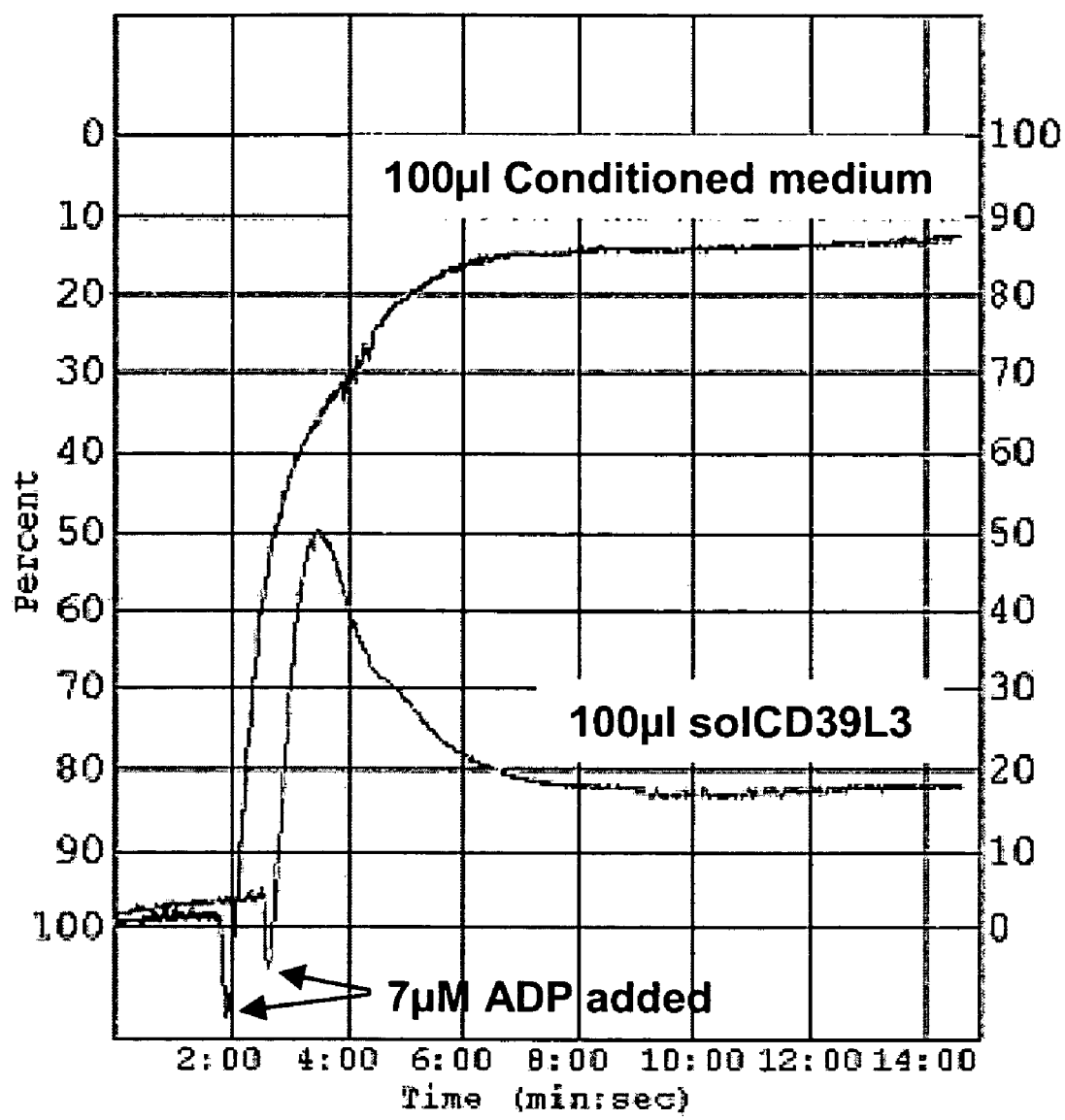
FIG. 16 is a graph demonstrating the inhibition of ADP-induced platelet reactivity by soluble CD39L3.

Platelet-rich plasma (PRP) was prepared by removing red blood cells and white blood cells by centrifugation from the donor's blood (Gayle III et al. (1998) *J. Clinical Investigation* 101:1851-1859). The PRP was preincubated for 3 minutes at 37° C. in an aggregometer cuvette (Lumiaggregometer; Chrono-Log, Harvertown, Pa.) in combination with test samples containing 100 µl of mock transfected conditioned medium or 100 µl of solCD39L3. Total volumes were adjusted to 300 µl with TSG buffer. After the 3-min preincubation, 7 µM ADP was added and the aggregation response was recorded for 4-5 minutes (FIG. 16). Platelet aggregation reactivity by ADP addition was inhibited by solCD39L3 ADPase activity, whereas aggregation was remained with conditioned medium (FIG. 16).

The invention claimed is:

1. An isolated polypeptide consisting of an amino acid sequence at least 95% identical to positions 44-484 of SEQ ID NO:20 and which has apyrase activity.

2. The polypeptide of claim 1, which consists of an amino acid sequence at least 99% identical to positions 44-484 of SEQ ID NO: 20.

3. The polypeptide of claim 2, which consists of the amino acid sequence of positions 44-484 of SEQ ID NO: 20.

4. The polypeptide of claim 1, which consists of the amino acid sequence of positions 45-486 of SEQ ID NO: 20.

5. A pharmaceutical or veterinary composition comprising the polypeptide of claim 1, in admixture with a pharmaceutically acceptable carrier.

6. The composition of claim 5, wherein said pharmaceutically acceptable carrier comprises liposomes.

7. A pharmaceutical or veterinary composition comprising the polypeptide of claim 2, in admixture with a pharmaceutically acceptable carrier.

8. A pharmaceutical or veterinary composition comprising the polypeptide of claim 3, in admixture with a pharmaceutically acceptable carrier.

9. A pharmaceutical or veterinary composition comprising the polypeptide of claim 4, in admixture with a pharmaceutically acceptable carrier.

10. A method to inhibit the onset of, or to ameliorate the effects of a thrombotic disorder in a subject, which method comprises administering to a subject in need of such inhibition or amelioration an effective amount of the polypeptide of claim 1, wherein said thrombotic disorder is stroke, coronary artery disease or injury resulting from myocardial infarction; atherosclerosis; arteriosclerosis; embolism; preeclampsia; angioplasty; vessel injury; transplantation; neonatal hypoxic ischemic encephalopathy; platelet-associated ischemic disorders including lung ischemia; coronary ischemia and cerebral ischemia; coronary artery thrombosis; cerebral artery thrombosis; intracardiac thrombosis; peripheral artery thrombosis; and venous thrombosis.

11. The method of claim 10, wherein said thrombotic disorder is stroke.

12. The method of claim 10, wherein said polypeptide is coupled to a label, a targeting agent, or a moiety that affects biological half-life.

13. A method to inhibit the onset of, or to ameliorate the effects of a thrombotic disorder in a subject, which method comprises administering to a subject in need of such inhibition or amelioration an effective amount of the polypeptide of claim 2, wherein said thrombotic disorder is stroke, coronary artery disease or injury resulting from myocardial infarction; atherosclerosis; arteriosclerosis; embolism; preeclampsia; angioplasty; vessel injury; transplantation; neonatal hypoxic ischemic encephalopathy; platelet-associated ischemic disorders including lung ischemia; coronary ischemia and cerebral ischemia; coronary artery thrombosis;

cerebral artery thrombosis; intracardiac thrombosis; peripheral artery thrombosis; and venous thrombosis.

14. A method to inhibit the onset of, or to ameliorate the effects of a thrombotic disorder in a subject, which method comprises administering to a subject in need of such inhibition or amelioration an effective amount of the polypeptide of claim 3, wherein said thrombotic disorder is stroke, coronary artery disease or injury resulting from myocardial infarction; atherosclerosis; arteriosclerosis; embolism; preeclampsia; angioplasty; vessel injury; transplantation; neonatal hypoxic ischemic encephalopathy; platelet-associated ischemic disorders including lung ischemia; coronary ischemia and cerebral ischemia; coronary artery thrombosis; cerebral artery thrombosis; intracardiac thrombosis; peripheral artery thrombosis; and venous thrombosis.

15. A method to inhibit the onset of, or to ameliorate the effects of a thrombotic disorder in a subject, which method comprises administering to a subject in need of such inhibition or amelioration an effective amount of the polypeptide of claim 4, wherein said thrombotic disorder is stroke, coronary artery disease or injury resulting from myocardial infarction; atherosclerosis; arteriosclerosis; embolism; preeclampsia; angioplasty; vessel injury; transplantation; neonatal hypoxic ischemic encephalopathy; platelet-associated ischemic disorders including lung ischemia; coronary ischemia and cerebral ischemia; coronary artery thrombosis; cerebral artery thrombosis; intracardiac thrombosis; peripheral artery thrombosis; and venous thrombosis.

\* \* \* \* \*

SEQUENCE LISTING

```
<160> NUMBER OF SEQ ID NOS: 30

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
ttggatccat ggtcactgtg ctgacccgcc                                    30

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
ttggatccat ggagatccac aagcaagagg                                    30

<210> SEQ ID NO 3
<211> LENGTH: 38
<212> TYPE: DNA
<213> ORGANISM: Artificial Sequence
<220> FEATURE:
<223> OTHER INFORMATION: Primer

<400> SEQUENCE: 3
```

```
cctcgaggat cctatcagtc agaatccact gcatggtc                    38

<210> SEQ ID NO 4
<211> LENGTH: 38
<212> TYPE: DNA
<213> ORGANISM: Artificial Sequence
<220> FEATURE:
<223> OTHER INFORMATION: Primer

<400> SEQUENCE: 4
cctcgaggat cctatcagac aggtggttct atgggcag                    38

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ccggagtggt cagtcaaacc                                        20

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6 gcccttttgac tttagggg                                         18

<210> SEQ ID NO 7
<211> LENGTH: 16
<212> TYPE: DNA
<213> ORGANISM: Artificial Sequence
<220> FEATURE:
<223> OTHER INFORMATION: Primer

<400> SEQUENCE: 7
ggctacgtat acacgc                                            16

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
ggtggcttcc atatttgac                                         19

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
gatgaggtat atgcccgc                                          18

<210> SEQ ID NO 10
<211> LENGTH: 18
<212> TYPE: DNA
```

```
<213> ORGANISM: Artificial Sequence
<220> FEATURE:
<223> OTHER INFORMATION: Primer

<400> SEQUENCE: 10
gcgggcatat acctcatc                                                      18

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
gtcaaatatg gaagccacc                                                     19

<210> SEQ ID NO 12
<211> LENGTH: 16
<212> TYPE: DNA
<213> ORGANISM: Artificial Sequence
<220> FEATURE:
<223> OTHER INFORMATION: Primer

<400> SEQUENCE: 12
gcgtgtatac gtagcc                                                        16

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
taaagtcaaa gggctggg                                                      18

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ggtttgactg accactccgg                                                    20

<210> SEQ ID NO 15
<211> LENGTH: 39
<212> TYPE: DNA
<213> ORGANISM: Artificial Sequence
<220> FEATURE:
<223> OTHER INFORMATION: Primer

<400> SEQUENCE: 15 aaacccggg atgcagatcc acaagcaaga ggtcctccc                                39

<210> SEQ ID NO 16
<211> LENGTH: 35
<212> TYPE: DNA
<213> ORGANISM: Artificial Sequence
<220> FEATURE:
<223> OTHER INFORMATION: Primer

<400> SEQUENCE: 16 aaacccggg ctatcagaca ggtggttcta tgggc                                    35
```

<210> SEQ ID NO 17
<211> LENGTH: 36
<212> TYPE: DNA
<213> ORGANISM: Artificial Sequence
<220> FEATURE:
<223> OTHER INFORMATION: Primer

<400> SEQUENCE: 17
tccactggtg acgcgcccgg gccggccagg cgcgcc        36

<210> SEQ ID NO 18
<211> LENGTH: 36
<212> TYPE: DNA
<213> ORGANISM: Artificial Sequence
<220> FEATURE:
<223> OTHER INFORMATION: Primer

<400> SEQUENCE: 18
ggggcgcctg gccggcccgg gcgcgtcacc agtgga        36

<210> SEQ ID NO 19
<211> LENGTH: 1590
<212> TYPE: DNA
<213> ORGANISM: Homo sapiens

<400> SEQUENCE: 19

| | | | | | |
|---|---|---|---|---|---|
| atggtcactg | tgctgacccg | ccaaccatgt | gagcaagcag | gcctcaaggc | cctctaccga | 60 |
| actccaacca | tcattgcctt | ggtggtcttg | cttgtgagta | ttgtggtact | tgtgagtatc | 120 |
| actgtcatcc | agatccacaa | gcaagaggtc | ctccctccag | gactgaagta | tggtattgtg | 180 |
| ctggatgccg | ggtcttcaag | aaccacagtc | tacgtgtatc | aatggccagc | agaaaaagag | 240 |
| aataataccg | gagtggtcag | tcaaaccttc | aaatgtagtg | tgaaaggctc | tggaatctcc | 300 |
| agctatggaa | ataacccca | agatgtcccc | agagcctttg | aggagtgtat | gcaaaaagtc | 360 |
| aaggggcagg | ttccatccca | cctccacgga | tccaccccca | ttcacctggg | agccacggct | 420 |
| gggatgcgct | tgctgaggtt | gcaaaatgaa | acagcagcta | atgaagtcct | tgaaagcatc | 480 |
| caaagctact | tcaagtccca | gcctttgac | tttaggggtg | ctcaaatcat | ttctgggcaa | 540 |
| gaagaagggg | tatatggatg | gattacagcc | aactatttaa | tgggaaattt | cctggagaag | 600 |
| aacctgtggc | acatgtgggt | gcacccgcat | ggagtggaaa | ccacgggtgc | cctggactta | 660 |
| ggtggtgcct | ccacccaaat | atccttcgtg | gcaggagaga | agatggatct | gaacaccagc | 720 |
| gacatcatgc | aggtgtccct | gtatggctac | gtatacacgc | tctacacaca | cagcttccag | 780 |
| tgctatggcc | ggaatgaggc | tgagaagaag | tttctggcaa | tgctcctgca | gaattctcct | 840 |
| accaaaaacc | atctcaccaa | tcctgttac | cctcgggatt | atagcatcag | cttccacatg | 900 |
| ggccatgtat | ttgatagcct | gtgcactgtg | gaccagaggc | cagaaagtta | taaccccaat | 960 |
| gatgtcatca | cttttgaagg | aactggggac | ccatctctgt | gtaaggagaa | ggtggcttcc | 1020 |
| atatttgact | tcaaagcttg | ccatgatcaa | gaaacctgtt | cttttgatgg | ggtttatcag | 1080 |
| ccaaagatta | aagggccatt | tgtggctttt | gcaggattct | actacacagc | cagtgctttta | 1140 |
| aatctttcag | gtagcttttc | cctggacacc | ttcaactcca | gcacctggaa | tttctgctca | 1200 |
| cagaattgga | gtcagctccc | actgctgctc | cccaaatttg | atgaggtata | tgcccgctct | 1260 |
| tactgcttct | cagccaacta | catctaccac | ttgttttgtga | acggttacaa | attcacagag | 1320 |
| gagacttggc | cccaaataca | ctttgaaaaa | gaagtgggga | atagcagcat | agcctggtct | 1380 |

```
cttggctaca tgctcagcct gaccaaccag atcccagctg aaagccctct gatccgtctg    1440
cccatagaac cacctgtctt tgtgggcacc ctcgctttct tcacagcggc agccttgctg    1500
tgtctggcat tcttgcata cctgtgttca gcaaccagaa gaaagaggca ctccgagcat    1560
gcctttgacc atgcagtgga ttctgactga                                     1590
```

<210> SEQ ID NO 20
<211> LENGTH: 529
<212> TYPE: PRT
<213> ORGANISM: Homo sapiens

<400> SEQUENCE: 20

```
Met Val Thr Val Leu Thr Arg Gln Pro Cys Glu Gln Ala Gly Leu Lys
  1               5                  10                  15

Ala Leu Tyr Arg Thr Pro Thr Ile Ile Ala Leu Val Val Leu Leu Val
                 20                  25                  30

Ser Ile Val Val Leu Val Ser Ile Thr Val Ile Gln Ile His Lys Gln
         35                  40                  45

Glu Val Leu Pro Pro Gly Leu Lys Tyr Gly Ile Val Leu Asp Ala Gly
     50                  55                  60

Ser Ser Arg Thr Thr Val Tyr Val Tyr Gln Trp Pro Ala Glu Lys Glu
 65                  70                  75                  80

Asn Asn Thr Gly Val Val Ser Gln Thr Phe Lys Cys Ser Val Lys Gly
                 85                  90                  95

Ser Gly Ile Ser Ser Tyr Gly Asn Asn Pro Gln Asp Val Pro Arg Ala
            100                 105                 110

Phe Glu Glu Cys Met Gln Lys Val Lys Gly Gln Val Pro Ser His Leu
        115                 120                 125

His Gly Ser Thr Pro Ile His Leu Gly Ala Thr Ala Gly Met Arg Leu
    130                 135                 140

Leu Arg Leu Gln Asn Glu Thr Ala Ala Asn Glu Val Leu Glu Ser Ile
145                 150                 155                 160

Gln Ser Tyr Phe Lys Ser Gln Pro Phe Asp Phe Arg Gly Ala Gln Ile
                165                 170                 175

Ile Ser Gly Gln Glu Glu Gly Val Tyr Gly Trp Ile Thr Ala Asn Tyr
            180                 185                 190

Leu Met Gly Asn Phe Leu Glu Lys Asn Leu Trp His Met Trp Val His
        195                 200                 205

Pro His Gly Val Glu Thr Thr Gly Ala Leu Asp Leu Gly Gly Ala Ser
    210                 215                 220

Thr Gln Ile Ser Phe Val Ala Gly Glu Lys Met Asp Leu Asn Thr Ser
225                 230                 235                 240

Asp Ile Met Gln Val Ser Leu Tyr Gly Tyr Val Tyr Thr Leu Tyr Thr
                245                 250                 255

His Ser Phe Gln Cys Tyr Gly Arg Asn Glu Ala Glu Lys Lys Phe Leu
            260                 265                 270

Ala Met Leu Leu Gln Asn Ser Pro Thr Lys Asn His Leu Thr Asn Pro
        275                 280                 285

Cys Tyr Pro Arg Asp Tyr Ser Ile Ser Phe Thr Met Gly His Val Phe
    290                 295                 300

Asp Ser Leu Cys Thr Val Asp Gln Arg Pro Glu Ser Tyr Asn Pro Asn
305                 310                 315                 320

Asp Val Ile Thr Phe Glu Gly Thr Gly Asp Pro Ser Leu Cys Lys Glu
                325                 330                 335
```

```
Lys Val Ala Ser Ile Phe Asp Phe Lys Ala Cys His Asp Gln Glu Thr
                340                 345                 350
Cys Ser Phe Asp Gly Val Tyr Gln Pro Lys Ile Lys Gly Pro Phe Val
            355                 360                 365
Ala Phe Ala Gly Phe Tyr Tyr Thr Ala Ser Ala Leu Asn Leu Ser Gly
        370                 375                 380
Ser Phe Ser Leu Asp Thr Phe Asn Ser Ser Thr Trp Asn Phe Cys Ser
385                 390                 395                 400
Gln Asn Trp Ser Gln Leu Pro Leu Leu Leu Pro Lys Phe Asp Glu Val
                405                 410                 415
Tyr Ala Arg Ser Tyr Cys Phe Ser Ala Asn Tyr Ile Tyr His Leu Phe
                420                 425                 430
Val Asn Gly Tyr Lys Phe Thr Glu Glu Thr Trp Pro Gln Ile His Phe
            435                 440                 445
Glu Lys Glu Val Gly Asn Ser Ser Ile Ala Trp Ser Leu Gly Tyr Met
        450                 455                 460
Leu Ser Leu Thr Asn Gln Ile Pro Ala Glu Ser Pro Leu Ile Arg Leu
465                 470                 475                 480
Pro Ile Glu Pro Pro Val Phe Val Gly Thr Leu Ala Phe Phe Thr Ala
                485                 490                 495
Ala Ala Leu Leu Cys Leu Ala Phe Leu Ala Tyr Leu Cys Ser Ala Thr
                500                 505                 510
Arg Arg Lys Arg His Ser Glu His Ala Phe Asp His Ala Val Asp Ser
            515                 520                 525
Asp
```

<210> SEQ ID NO 21
<211> LENGTH: 1335
<212> TYPE: DNA
<213> ORGANISM: Homo sapiens

<400> SEQUENCE: 21

```
atggagatcc acaagcaaga ggtcctccct ccaggactga agtatggtat tgtgctggat     60
gccgggtctt caagaaccac agtctacgtg tatcaatggc agcagaaaa agagaataat    120
accggagtgg tcagtcaaac cttcaaatgt agtgtgaaag ctctggaat ctccagctat    180
ggaaataacc cccaagatgt ccccagagcc tttgaggagt gtatgcaaaa agtcaagggg    240
caggttccat cccacctcca cggatccacc cccattcacc tgggagccac ggctgggatg    300
cgcttgctga ggttgcaaaa tgaaacagca gctaatgaag tccttgaaag catccaaagc    360
tacttcaagt cccagccctt tgactttagg ggtgctcaaa tcatttctgg caagaagaa    420
ggggtatatg gatggattac agccaactat ttaatggaaa atttcctgga agaacctg    480
tggcacatgt gggtgcaccc gcatggagtg gaaaccacgg gtgccctgga cttaggtggt    540
gcctccaccc aaatatcctt cgtggcagga gagaagatga tctgaacac agcgacatc    600
atgcaggtgt ccctgtatgg ctacgtatac acgctctaca cacagcttt ccagtgctat    660
ggccggaatg aggctgagaa gaagtttctg caatgctcc tgcagaattc tcctaccaaa    720
aaccatctca ccaatccctg ttaccctcgg gattatagca tcagcttcac catgggccat    780
gtatttgata gcctgtgcac tgtggaccag aggccagaaa gttataaccc caatgatgtc    840
atcacttttg aaggaactgg ggacccatct ctgtgtaagg agaaggtggc ttccatattt    900
gacttcaaag cttgccatga tcaagaaacc tgttctttg atggggttta tcagccaaag    960
attaaagggc catttgtggc ttttgcagga ttctactaca cagccagtgc tttaaatctt   1020
```

-continued

```
tcaggtagct tttccctgga caccttcaac tccagcacct ggaatttctg ctcacagaat    1080
tggagtcagc tcccactgct gctccccaaa tttgatgagg tatatgcccg ctcttactgc    1140
ttctcagcca actacatcta ccacttgttt gtgaacggtt acaaattcac agaggagact    1200 tggcccaaa tacactttga aaagaagtg gggaatagca gcatagcctg gtctcttggc      1260
tacatgctca gcctgaccaa ccagatccca gctgaaagcc ctctgatccg tctgcccata    1320
gaaccacctg tctga                                                     1335
```

<210> SEQ ID NO 22
<211> LENGTH: 444
<212> TYPE: PRT
<213> ORGANISM: Homo sapiens

<400> SEQUENCE: 22

```
Met Glu Ile His Lys Gln Glu Val Leu Pro Gly Leu Lys Tyr Gly
  1               5                  10                  15

Ile Val Leu Asp Ala Gly Ser Ser Arg Thr Thr Val Tyr Val Tyr Gln
                 20                  25                  30

Trp Pro Ala Glu Lys Glu Asn Asn Thr Gly Val Val Ser Gln Thr Phe
             35                  40                  45

Lys Cys Ser Val Lys Gly Ser Gly Ile Ser Ser Tyr Gly Asn Asn Pro
 50                  55                  60

Gln Asp Val Pro Arg Ala Phe Glu Glu Cys Met Gln Lys Val Lys Gly
 65                  70                  75                  80

Gln Val Pro Ser His Leu His Gly Ser Thr Pro Ile His Leu Gly Ala
                 85                  90                  95

Thr Ala Gly Met Arg Leu Leu Arg Leu Gln Asn Glu Thr Ala Ala Asn
                100                 105                 110

Glu Val Leu Glu Ser Ile Gln Ser Tyr Phe Lys Ser Gln Pro Phe Asp
            115                 120                 125

Phe Arg Gly Ala Gln Ile Ile Ser Gly Gln Glu Glu Gly Val Tyr Gly
130                 135                 140

Trp Ile Thr Ala Asn Tyr Leu Met Gly Asn Phe Leu Glu Lys Asn Leu
145                 150                 155                 160

Trp His Met Trp Val His Pro His Gly Val Glu Thr Thr Gly Ala Leu
                165                 170                 175

Asp Leu Gly Gly Ala Ser Thr Gln Ile Ser Phe Val Ala Gly Glu Lys
            180                 185                 190

Met Asp Leu Asn Thr Ser Asp Ile Met Gln Val Ser Leu Tyr Gly Tyr
            195                 200                 205

Val Tyr Thr Leu Tyr Thr His Ser Phe Gln Cys Tyr Gly Arg Asn Glu
            210                 215                 220

Ala Glu Lys Lys Phe Leu Ala Met Leu Leu Gln Asn Ser Pro Thr Lys
225                 230                 235                 240

Asn His Leu Thr Asn Pro Cys Tyr Pro Arg Asp Tyr Ser Ile Ser Phe
                245                 250                 255

Thr Met Gly His Val Phe Asp Ser Leu Cys Thr Val Asp Gln Arg Pro
            260                 265                 270

Glu Ser Tyr Asn Pro Asn Asp Val Ile Thr Phe Glu Gly Thr Gly Asp
            275                 280                 285

Pro Ser Leu Cys Lys Glu Lys Val Ala Ser Ile Phe Asp Phe Lys Ala
        290                 295                 300

Cys His Asp Gln Glu Thr Cys Ser Phe Asp Gly Val Tyr Gln Pro Lys
```

```
             305                 310                 315                 320
Ile Lys Gly Pro Phe Val Ala Phe Ala Gly Phe Tyr Tyr Thr Ala Ser
                325                 330                 335
Ala Leu Asn Leu Ser Gly Ser Phe Ser Leu Asp Thr Phe Asn Ser Ser
                340                 345                 350
Thr Trp Asn Phe Cys Ser Gln Asn Trp Ser Gln Leu Pro Leu Leu Leu
                355                 360                 365
Pro Lys Phe Asp Glu Val Tyr Ala Arg Ser Tyr Cys Phe Ser Ala Asn
            370                 375                 380
Tyr Ile Tyr His Leu Phe Val Asn Gly Tyr Lys Phe Thr Glu Glu Thr
385                 390                 395                 400
Trp Pro Gln Ile His Phe Glu Lys Glu Val Gly Asn Ser Ser Ile Ala
                405                 410                 415
Trp Ser Leu Gly Tyr Met Leu Ser Leu Thr Asn Gln Ile Pro Ala Glu
                420                 425                 430
Ser Pro Leu Ile Arg Leu Pro Ile Glu Pro Pro Val
            435                 440

<210> SEQ ID NO 23
<211> LENGTH: 1338
<212> TYPE: DNA
<213> ORGANISM: Homo sapiens

<400> SEQUENCE: 23
atgcagatcc acaagcaaga ggtcctccct ccaggactga agtatggtat tgtgctggat      60
gccgggtctt caagaaccac agtctacgtg tatcaatggc cagcagaaaa agagaataat    120
accggagtgg tcagtcaaac cttcaaatgt agtgtgaaag ctctggaat ctccagctat     180 ggaaataacc cccaagatgt ccccagagcc tttgaggagt gtatgcaaaa agtcaagggg    240
caggttccat cccacctcca cggatccacc cccattcacc tgggagccac ggctgggatg    300
cgcttgctga ggttgcaaaa tgaaacagca gctaatgaag tccttgaaag catccaaagc    360
tacttcaagt cccagccctt tgactttagg ggtgctcaaa tcatttctgg caagaagaa     420 ggggtatatg gatggattac agccaactat ttaatgggaa atttcctgga agagaacctg    480
tggcacatgt gggtgcaccc gcatggagtg gaaaccacgg tgccctgga cttaggtggt     540 gcctccaccc aaatatcctt cgtggcagga gagaagatgg atctgaacac cagcgacatc    600
atgcaggtgt ccctgtatgg ctacgtatac acgctctaca cacacagctt ccagtgctat    660
ggccggaatg aggctgagaa gagtttctg gcaatgctcc tgcagaattc tcctaccaaa     720
aaccatctca ccaatccctg ttaccctcgg gattatagca tcagcttcac catgggccat    780
gtatttgata gcctgtgcac tgtggaccag aggccagaaa gttataaccc caatgatgtc    840 atcactttg aaggaactgg ggacccatct ctgtgtaagg agaaggtggc ttccatattt    900
gacttcaaag cttgccatga tcaagaaacc tgttcttttg atggggttta tcagccaaag    960
attaaagggc catttgtggc ttttgcagga ttctactaca cagccagtgc tttaaatctt   1020
tcaggtagct tttccctgga caccttcaac tccagcacct ggaatttctg ctcacagaat   1080
tggagtcagc tcccactgct gctccccaaa tttgatgagg tatatgcccg ctcttactgc   1140
ttctcagcca actacatcta ccacttgttt gtgaacggtt acaaattcac agaggagact   1200
tggccccaaa tacactttga aaaagaagtg gggaatagca gcatagcctg gtctcttggc   1260
tacatgctca gcctgaccaa ccagatccca gctgaaagcc ctctgatccg tctgcccata   1320
gaaccacctg tctgatag                                                 1338
```

<210> SEQ ID NO 24
<211> LENGTH: 444
<212> TYPE: PRT
<213> ORGANISM: Homo sapiens

<400> SEQUENCE: 24

```
Met Gln Ile His Lys Gln Glu Val Leu Pro Gly Leu Lys Tyr Gly
 1               5                  10                  15

Ile Val Leu Asp Ala Gly Ser Ser Arg Thr Thr Val Tyr Val Tyr Gln
                20                  25                  30

Trp Pro Ala Glu Lys Glu Asn Thr Gly Val Val Ser Gln Thr Phe
            35                  40                  45

Lys Cys Ser Val Lys Gly Ser Gly Ile Ser Ser Tyr Gly Asn Asn Pro
 50                  55                  60

Gln Asp Val Pro Arg Ala Phe Glu Glu Cys Met Gln Lys Val Lys Gly
 65                  70                  75                  80

Gln Val Pro Ser His Leu His Gly Ser Thr Pro Ile His Leu Gly Ala
                85                  90                  95

Thr Ala Gly Met Arg Leu Leu Arg Leu Gln Asn Glu Thr Ala Ala Asn
                100                 105                 110

Glu Val Leu Glu Ser Ile Gln Ser Tyr Phe Lys Ser Gln Pro Phe Asp
                115                 120                 125

Phe Arg Gly Ala Gln Ile Ile Ser Gly Gln Glu Glu Gly Val Tyr Gly
            130                 135                 140

Trp Ile Thr Ala Asn Tyr Leu Met Gly Asn Phe Leu Glu Lys Asn Leu
145                 150                 155                 160

Trp His Met Trp Val His Pro His Gly Val Glu Thr Thr Gly Ala Leu
                165                 170                 175

Asp Leu Gly Gly Ala Ser Thr Gln Ile Ser Phe Val Ala Gly Glu Lys
                180                 185                 190

Met Asp Leu Asn Thr Ser Asp Ile Met Gln Val Ser Leu Tyr Gly Tyr
                195                 200                 205

Val Tyr Thr Leu Tyr Thr His Ser Phe Gln Cys Tyr Gly Arg Asn Glu
                210                 215                 220

Ala Glu Lys Lys Phe Leu Ala Met Leu Leu Gln Asn Ser Pro Thr Lys
225                 230                 235                 240

Asn His Leu Thr Asn Pro Cys Tyr Pro Arg Asp Tyr Ser Ile Ser Phe
                245                 250                 255

Thr Met Gly His Val Phe Asp Ser Leu Cys Thr Val Asp Gln Arg Pro
                260                 265                 270

Glu Ser Tyr Asn Pro Asn Asp Val Ile Thr Phe Glu Gly Thr Gly Asp
                275                 280                 285

Pro Ser Leu Cys Lys Glu Lys Val Ala Ser Ile Phe Asp Phe Lys Ala
            290                 295                 300

Cys His Asp Gln Glu Thr Cys Ser Phe Asp Gly Val Tyr Gln Pro Lys
305                 310                 315                 320

Ile Lys Gly Pro Phe Val Ala Phe Ala Gly Phe Tyr Tyr Thr Ala Ser
                325                 330                 335

Ala Leu Asn Leu Ser Gly Ser Phe Ser Leu Asp Thr Phe Asn Ser Ser
                340                 345                 350

Thr Trp Asn Phe Cys Ser Gln Asn Trp Ser Gln Leu Pro Leu Leu Leu
                355                 360                 365

Pro Lys Phe Asp Glu Val Tyr Ala Arg Ser Tyr Cys Phe Ser Ala Asn
```

```
                370             375             380
Tyr Ile Tyr His Leu Phe Val Asn Gly Tyr Lys Phe Thr Glu Glu Thr
385                     390                     395                 400

Trp Pro Gln Ile His Phe Glu Lys Glu Val Gly Asn Ser Ser Ile Ala
                405                     410                 415

Trp Ser Leu Gly Tyr Met Leu Ser Leu Thr Asn Gln Ile Pro Ala Glu
                420                     425                 430

Ser Pro Leu Ile Arg Leu Pro Ile Glu Pro Pro Val
                435                     440

<210> SEQ ID NO 25
<211> LENGTH: 448
<212> TYPE: PRT
<213> ORGANISM: Homo sapiens

<400> SEQUENCE: 25

Asp Ala Pro Gly Met Gln Ile His Lys Gln Glu Val Leu Pro Pro Gly
1               5                   10                  15

Leu Lys Tyr Gly Ile Val Leu Asp Ala Gly Ser Ser Arg Thr Thr Val
                20                  25                  30

Tyr Val Tyr Gln Trp Pro Ala Glu Lys Glu Asn Asn Thr Gly Val Val
            35                  40                  45

Ser Gln Thr Phe Lys Cys Ser Val Lys Gly Ser Gly Ile Ser Ser Tyr
    50                  55                  60

Gly Asn Asn Pro Gln Asp Val Pro Arg Ala Phe Glu Glu Cys Met Gln
65                  70                  75                  80

Lys Val Lys Gly Gln Val Pro Ser His Leu His Gly Ser Thr Pro Ile
                85                  90                  95

His Leu Gly Ala Thr Ala Gly Met Arg Leu Leu Arg Leu Gln Asn Glu
            100                 105                 110

Thr Ala Ala Asn Glu Val Leu Glu Ser Ile Gln Ser Tyr Phe Lys Ser
        115                 120                 125

Gln Pro Phe Asp Phe Arg Gly Ala Gln Ile Ile Ser Gly Gln Glu Glu
    130                 135                 140

Gly Val Tyr Gly Trp Ile Thr Ala Asn Tyr Leu Met Gly Asn Phe Leu
145                 150                 155                 160

Glu Lys Asn Leu Trp His Met Trp Val His Pro His Gly Val Glu Thr
                165                 170                 175

Thr Gly Ala Leu Asp Leu Gly Gly Ala Ser Thr Gln Ile Ser Phe Val
            180                 185                 190

Ala Gly Glu Lys Met Asp Leu Asn Thr Ser Asp Ile Met Gln Val Ser
        195                 200                 205

Leu Tyr Gly Tyr Val Tyr Thr Leu Tyr Thr His Ser Phe Gln Cys Tyr
    210                 215                 220

Gly Arg Asn Glu Ala Glu Lys Lys Phe Leu Ala Met Leu Leu Gln Asn
225                 230                 235                 240

Ser Pro Thr Lys Asn His Leu Thr Asn Pro Cys Tyr Pro Arg Asp Tyr
                245                 250                 255

Ser Ile Ser Phe Thr Met Gly His Val Phe Asp Ser Leu Cys Thr Val
            260                 265                 270

Asp Gln Arg Pro Glu Ser Tyr Asn Pro Asn Asp Val Ile Thr Phe Glu
        275                 280                 285

Gly Thr Gly Asp Pro Ser Leu Cys Lys Glu Lys Val Ala Ser Ile Phe
    290                 295                 300
```

Asp Phe Lys Ala Cys His Asp Gln Glu Thr Cys Ser Phe Asp Gly Val
305                 310                 315                 320

Tyr Gln Pro Lys Ile Lys Gly Pro Phe Val Ala Phe Ala Gly Phe Tyr
            325                 330                 335

Tyr Thr Ala Ser Ala Leu Asn Leu Ser Gly Ser Phe Ser Leu Asp Thr
        340                 345                 350

Phe Asn Ser Ser Thr Trp Asn Phe Cys Ser Gln Asn Trp Ser Gln Leu
    355                 360                 365

Pro Leu Leu Pro Lys Phe Asp Glu Val Tyr Ala Arg Ser Tyr Cys
370                 375                 380

Phe Ser Ala Asn Tyr Ile Tyr His Leu Phe Val Asn Gly Tyr Lys Phe
385                 390                 395                 400

Thr Glu Glu Thr Trp Pro Gln Ile His Phe Glu Lys Glu Val Gly Asn
                405                 410                 415

Ser Ser Ile Ala Trp Ser Leu Gly Tyr Met Leu Ser Leu Thr Asn Gln
            420                 425                 430

Ile Pro Ala Glu Ser Pro Leu Ile Arg Leu Pro Ile Glu Pro Pro Val
            435                 440                 445

<210> SEQ ID NO 26
<211> LENGTH: 517
<212> TYPE: PRT
<213> ORGANISM: Homo sapiens

<400> SEQUENCE: 26

Met Lys Gly Thr Lys Asp Leu Thr Ser Gln Gln Lys Glu Ser Asn Val
1               5                   10                  15

Lys Thr Phe Cys Ser Lys Asn Ile Leu Ala Ile Leu Gly Phe Ser Ser
            20                  25                  30

Ile Ile Ala Val Ile Ala Leu Leu Ala Val Gly Leu Thr Gln Asn Lys
        35                  40                  45

Ala Leu Pro Glu Asn Val Lys Tyr Gly Ile Val Leu Asp Ala Gly Ser
    50                  55                  60

Ser His Thr Ser Leu Tyr Ile Tyr Lys Trp Pro Ala Glu Lys Glu Asn
65                  70                  75                  80

Asp Thr Gly Val Val His Gln Val Glu Glu Cys Arg Val Lys Gly Pro
                85                  90                  95

Gly Ile Ser Lys Phe Val Gln Lys Val Asn Glu Ile Gly Ile Tyr Leu
            100                 105                 110

Thr Asp Cys Met Glu Arg Ala Arg Glu Val Ile Pro Arg Ser Gln His
        115                 120                 125

Gln Glu Thr Pro Val Tyr Leu Gly Ala Thr Ala Gly Met Arg Leu Leu
    130                 135                 140

Arg Met Glu Ser Glu Glu Leu Ala Asp Arg Val Leu Asp Val Val Glu
145                 150                 155                 160

Arg Ser Leu Ser Asn Tyr Pro Phe Asp Phe Gln Gly Ala Arg Ile Ile
                165                 170                 175

Thr Gly Gln Glu Glu Gly Ala Tyr Gly Trp Ile Thr Ile Asn Tyr Leu
            180                 185                 190

Leu Gly Lys Phe Ser Gln Lys Thr Arg Trp Phe Ser Ile Val Pro Tyr
        195                 200                 205

Glu Thr Asn Asn Gln Glu Thr Phe Gly Ala Leu Asp Leu Gly Gly Ala
    210                 215                 220

Ser Thr Gln Val Thr Phe Val Pro Gln Asn Gln Thr Ile Glu Ser Pro
225                 230                 235                 240

```
Asp Asn Ala Leu Gln Phe Arg Leu Tyr Gly Lys Asp Tyr Asn Val Tyr
            245                 250                 255

Thr His Ser Phe Leu Cys Tyr Gly Lys Asp Gln Ala Leu Trp Gln Lys
            260                 265                 270

Leu Ala Lys Asp Ile Gln Val Ala Ser Asn Glu Ile Leu Arg Asp Pro
            275                 280                 285

Cys Phe His Pro Gly Tyr Lys Lys Val Asn Val Ser Asp Leu Tyr
            290                 295                 300

Lys Thr Pro Cys Thr Lys Arg Phe Glu Met Thr Leu Pro Phe Gln Gln
305                 310                 315                 320

Phe Glu Ile Gln Gly Ile Gly Asn Tyr Gln Gln Cys His Gln Ser Ile
            325                 330                 335

Leu Glu Leu Phe Asn Thr Ser Tyr Cys Pro Tyr Ser Gln Cys Ala Phe
            340                 345                 350

Asn Gly Ile Phe Leu Pro Pro Leu Gln Gly Asp Phe Gly Ala Phe Ser
            355                 360                 365

Ala Phe Tyr Phe Val Met Lys Phe Leu Asn Leu Thr Ser Glu Lys Val
            370                 375                 380

Ser Gln Glu Lys Val Thr Glu Met Met Lys Lys Phe Cys Ala Gln Pro
385                 390                 395                 400

Trp Glu Glu Ile Lys Thr Ser Tyr Ala Gly Val Lys Glu Lys Tyr Leu
            405                 410                 415

Ser Glu Tyr Cys Phe Ser Gly Thr Tyr Ile Leu Ser Leu Leu Leu Gln
            420                 425                 430

Gly Tyr His Phe Thr Ala Asp Ser Trp Glu His Ile His Phe Ile Gly
            435                 440                 445

Lys Ile Gln Gly Ser Asp Ala Gly Trp Thr Leu Gly Tyr Met Leu Asn
            450                 455                 460

Leu Thr Asn Met Ile Pro Ala Glu Gln Pro Leu Ser Thr Pro Leu Ser
465                 470                 475                 480

His Ser Thr Tyr Val Phe Leu Met Val Leu Phe Ser Leu Val Leu Phe
            485                 490                 495

Thr Val Ala Ile Ile Gly Leu Leu Ile Phe His Lys Pro Ser Tyr Phe
            500                 505                 510

Trp Lys Asp Met Val
            515

<210> SEQ ID NO 27
<211> LENGTH: 529
<212> TYPE: PRT
<213> ORGANISM: Homo sapiens

<400> SEQUENCE: 27

Met Phe Thr Val Leu Thr Arg Gln Pro Cys Glu Gln Ala Gly Leu Lys
1               5                   10                  15

Ala Leu Tyr Arg Thr Pro Thr Ile Ile Ala Leu Val Val Leu Leu Val
            20                  25                  30

Ser Ile Val Val Leu Val Ser Ile Thr Val Ile Gln Ile His Lys Gln
            35                  40                  45

Glu Val Leu Pro Pro Gly Leu Lys Tyr Gly Ile Val Leu Asp Ala Gly
            50                  55                  60

Ser Ser Arg Thr Thr Val Tyr Val Tyr Gln Trp Pro Ala Glu Lys Glu
65                  70                  75                  80

Asn Asn Thr Gly Val Val Ser Gln Thr Phe Lys Cys Ser Val Lys Gly
```

-continued

```
                85                  90                  95
Ser Gly Ile Ser Ser Tyr Gly Asn Asn Pro Gln Asp Val Pro Arg Ala
            100                 105                 110
Phe Glu Glu Cys Met Gln Lys Val Lys Gly Gln Val Pro Ser His Leu
            115                 120                 125
His Gly Ser Thr Pro Ile His Leu Gly Ala Thr Ala Gly Met Arg Leu
            130                 135                 140
Leu Arg Leu Gln Asn Glu Thr Ala Ala Asn Glu Val Leu Glu Ser Ile
145                 150                 155                 160
Gln Ser Tyr Phe Lys Ser Gln Pro Phe Asp Phe Arg Gly Ala Gln Ile
                165                 170                 175
Ile Ser Gly Gln Glu Glu Gly Val Tyr Gly Trp Ile Thr Ala Asn Tyr
            180                 185                 190
Leu Met Gly Asn Phe Leu Glu Lys Asn Leu Trp His Met Trp Val His
            195                 200                 205
Pro His Gly Val Glu Thr Thr Gly Ala Leu Asp Leu Gly Gly Ala Ser
            210                 215                 220
Thr Gln Ile Ser Phe Val Ala Gly Glu Lys Met Asp Leu Asn Thr Ser
225                 230                 235                 240
Asp Ile Met Gln Val Ser Leu Tyr Gly Tyr Val Tyr Thr Leu Tyr Thr
                245                 250                 255
His Ser Phe Gln Cys Tyr Gly Arg Asn Glu Ala Glu Lys Lys Phe Leu
            260                 265                 270
Ala Met Leu Leu Gln Asn Ser Pro Thr Lys Asn His Leu Thr Asn Pro
            275                 280                 285
Cys Tyr Pro Arg Asp Tyr Ser Ile Ser Phe Thr Met Gly His Val Phe
            290                 295                 300
Asp Ser Leu Cys Thr Val Asp Gln Arg Pro Glu Ser Tyr Asn Pro Asn
305                 310                 315                 320
Asp Val Ile Thr Phe Glu Gly Thr Gly Asp Pro Ser Leu Cys Lys Glu
                325                 330                 335
Lys Val Ala Ser Ile Phe Asp Phe Lys Ala Cys His Asp Gln Glu Thr
            340                 345                 350
Cys Ser Phe Asp Gly Val Tyr Gln Pro Lys Ile Lys Gly Pro Phe Val
            355                 360                 365
Ala Phe Ala Gly Phe Tyr Tyr Thr Ala Ser Ala Leu Asn Leu Ser Gly
            370                 375                 380
Ser Phe Ser Leu Asp Thr Phe Asn Ser Ser Thr Trp Asn Phe Cys Ser
385                 390                 395                 400
Gln Asn Trp Ser Gln Leu Pro Leu Leu Pro Lys Phe Asp Glu Val
                405                 410                 415
Tyr Ala Arg Ser Tyr Cys Phe Ser Ala Asn Tyr Ile Tyr His Leu Phe
            420                 425                 430
Val Asn Gly Tyr Lys Phe Thr Glu Glu Thr Trp Pro Gln Ile His Phe
            435                 440                 445
Glu Lys Glu Val Gly Asn Ser Ser Ile Ala Trp Ser Leu Gly Tyr Met
            450                 455                 460
Leu Ser Leu Thr Asn Gln Ile Pro Ala Glu Ser Pro Leu Ile Arg Leu
465                 470                 475                 480
Pro Ile Glu Pro Pro Val Phe Val Gly Thr Leu Ala Phe Phe Thr Val
                485                 490                 495
Ala Ala Leu Leu Cys Leu Ala Phe Leu Ala Tyr Leu Cys Ser Ala Thr
            500                 505                 510
```

```
-continued

Arg Arg Lys Arg His Ser Glu His Ala Phe Asp His Ala Val Asp Ser
        515                 520                 525

Asp

<210> SEQ ID NO 28
<211> LENGTH: 75
<212> TYPE: DNA
<213> ORGANISM: Homo sapiens

<400> SEQUENCE: 28
atggagacag acacactcct gctatgggta ctgctgctct gggttccagg ttccactggt      60
gacgcgcccg ggccg                                                      75

<210> SEQ ID NO 29
<211> LENGTH: 24
<212> TYPE: PRT
<213> ORGANISM: Homo sapiens

<400> SEQUENCE: 29

Met Glu Thr Asp Thr Leu Leu Leu Trp Val Leu Leu Leu Trp Val Pro
1               5                   10                  15

Gly Ser Thr Gly Asp Ala Pro Gly
            20

<210> SEQ ID NO 30
<211> LENGTH: 4
<212> TYPE: PRT
<213> ORGANISM: Homo sapiens

<400> SEQUENCE: 30

Asp Ala Pro Gly
1
```